United States Patent
Li

(12) 
(10) Patent No.: US 6,413,589 B1
(45) Date of Patent: *Jul. 2, 2002

(54) CERAMIC COATING METHOD

(76) Inventor: Chou H. Li, Unit 404, 8001 Sailboat Key Blvd., South Pasadena, FL (US) 33707

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/482,199

(22) Filed: Jun. 8, 1995

Related U.S. Application Data

(63) Continuation-in-part of application No. 08/301,582, filed on Sep. 7, 1994, now Pat. No. 5,874,175, which is a continuation-in-part of application No. 08/123,877, filed on Sep. 23, 1993, now Pat. No. 5,392,982, which is a continuation-in-part of application No. 07/804,287, filed on Dec. 9, 1991, now abandoned, and a continuation-in-part of application No. 07/804,285, filed on Dec. 9, 1991, now Pat. No. 5,248,079, and a continuation-in-part of application No. 07/644,421, filed on Jan. 22, 1991, now Pat. No. 5,230,624, said application No. 07/804,287, is a continuation-in-part of application No. 07/499,707, filed on Mar. 27, 1990, now Pat. No. 5,161,728, which is a continuation-in-part of application No. 07/277,666, filed on Nov. 29, 1988, now Pat. No. 4,890,783, said application No. 07/804,285, is a continuation-in-part of application No. 07/499,707, said application No. 07/644,421, is a continuation-in-part of application No. 07/277,672, filed on Dec. 14, 1988, now Pat. No. 5,000,986, said application No. 07/499,707, is a continuation-in-part of application No. 07/277,672.

(51) Int. Cl.$^7$ .............................. B05D 3/02; B05D 7/00

(52) U.S. Cl. ..................... 427/376.6; 427/193; 427/201; 427/203; 427/376.7; 427/419.7

(58) Field of Search ........................... 427/376.6, 376.7, 427/377, 404, 419.7, 201, 705, 193, 203

(56) References Cited

U.S. PATENT DOCUMENTS

| | | | | | |
|---|---|---|---|---|---|
| 2,163,407 A | * | 6/1939 | Pulfrich | .......................... | 18/59 |
| 2,570,248 A | * | 10/1951 | Kelley | ........................ | 29/179.5 |
| 2,667,432 A | * | 1/1954 | Nelte | .......................... | 117/123 |

(List continued on next page.)

FOREIGN PATENT DOCUMENTS

| | | |
|---|---|---|
| CA | 929738 | 7/1973 |
| EP | 0152624 | 8/1985 |
| JP | 6437870 | 2/1989 |

OTHER PUBLICATIONS

Mizuharo et al., "High–Reliability Joining of Ceramic to Metal," Ceramic Bulletin vol. 68 No. 9, 1989 pp 15–71–1599.*

Loehman et al., "Joining of Ceramics," Ceramic Bulletin vol. 67, No. 2, 1988 pp. 375–380.*

Pask, Ceramic Bulletin vol. 66 No. 11 1987 pp. 1587–1592.*

Handbook of Materials and Techniques for Vacuum Devices, pp. 456–466; published by Reinhold (1969).

U.S. application No. 08/301,582, Li, filed Sep. 7, 1994.

(List continued on next page.)

*Primary Examiner*—Michael Barr

(57) ABSTRACT

A method of coating a ceramic and bonding ceramic onto a substrate for practical uses over 630° C. includes forming a brazed bonding layer at a contact area between the ceramic and the substrate by a fluidic reaction and causing the bonding layer to wet both the ceramic and substrate with a wetting angle of 0–5° to thereby coat and bond the ceramic onto bond the substrate over the entire contact area with a continuous, essentially 100% dense bonding layer. The bonding layer is so free of bonding defects that the resulting bonded product can withstand repeated thermal shocks by quenching in 0° ice water from a temperature in the range of 630–980° C.

30 Claims, 2 Drawing Sheets

U.S. PATENT DOCUMENTS

| | | | |
|---|---|---|---|
| 2,708,787 A | * 5/1955 | Chick et al. | 29/473.1 |
| 3,215,555 A | 11/1965 | Krey | |
| 3,281,309 A | * 10/1966 | Ross | 161/196 |
| 3,428,846 A | * 2/1969 | Rigken et al. | 313/284 |
| 3,448,319 A | * 6/1969 | Louden | 313/221 |
| 3,574,579 A | 4/1971 | Clarke et al. | |
| 3,598,435 A | * 8/1971 | Jorgensen | 287/189.365 |
| 3,650,714 A | 3/1972 | Farkas | |
| 3,740,822 A | 6/1973 | Singleton | |
| 3,753,758 A | * 8/1973 | Shanley | 117/25 |
| 3,894,673 A | 7/1975 | Lowder et al. | |
| 3,901,772 A | * 8/1975 | Guillotin et al. | 204/16 |
| 3,915,369 A | 10/1975 | Schmidt-Bruecken et al. | |
| 3,949,263 A | 4/1976 | Harper | |
| 4,009,027 A | 2/1977 | Naidich et al. | |
| 4,018,576 A | 4/1977 | Lowder et al. | |
| 4,075,364 A | 2/1978 | Panzera | |
| 4,109,031 A | 8/1978 | Marscher | |
| 4,111,572 A | 9/1978 | Noone et al. | |
| 4,239,502 A | 12/1980 | Slack et al. | |
| 4,252,856 A | 2/1981 | Sara | |
| 4,338,380 A | 7/1982 | Erickson et al. | |
| 4,347,089 A | * 8/1982 | Lochman | 156/89 |
| 4,348,131 A | 9/1982 | Shimanuki et al. | |
| 4,396,677 A | 8/1983 | Intrater et al. | |
| 4,404,262 A | * 9/1983 | Watmough | 428/539.5 |
| 4,529,836 A | 7/1985 | Powers et al. | |
| 4,529,857 A | * 7/1985 | Meek et al. | 219/10.55 M |
| 4,556,389 A | * 12/1985 | Ueno et al. | 433/206 |
| 4,593,851 A | 6/1986 | Skog | |
| 4,608,226 A | 8/1986 | Lauvinerie | |
| 4,624,403 A | 11/1986 | Kohno et al. | |
| 4,703,884 A | 11/1987 | Landingham et al. | |
| 4,735,866 A | 4/1988 | Moorhead | |
| 4,750,914 A | 6/1988 | Chikaoka et al. | |
| 4,776,862 A | 10/1988 | Wiand | |
| 4,890,783 A | 1/1990 | Li | |
| 4,899,922 A | 2/1990 | Slutz et al. | |
| 4,924,033 A | 5/1990 | Iyogi et al. | |
| 4,953,499 A | 9/1990 | Anthony et al. | |
| 4,958,592 A | 9/1990 | Anthony et al. | |
| 4,968,326 A | 11/1990 | Wiand | |
| 4,970,986 A | 11/1990 | Anthony et al. | |
| 5,022,801 A | 6/1991 | Anthony et al. | |
| 5,110,579 A | 5/1992 | Anthony et al. | |
| 5,116,787 A | 5/1992 | Dumbaugh, Jr. | |
| 5,125,557 A | 6/1992 | Tanaka et al. | |
| 5,143,523 A | 9/1992 | Matarrese | |
| 5,161,728 A | 11/1992 | Li | |
| 5,190,823 A | 3/1993 | Anthony et al. | |
| 5,230,924 A | 7/1993 | Li | |
| 5,248,079 A | * 9/1993 | Li | 228/121 |
| 5,273,731 A | 12/1993 | Anthony et al. | |
| 5,349,922 A | 9/1994 | Anthony et al. | |
| 5,377,522 A | 1/1995 | Anthony et al. | |
| 5,392,982 A | 2/1995 | Li | |
| 5,419,276 A | 5/1995 | Anthony et al. | |
| 5,419,798 A | 5/1995 | Anthony et al. | |
| 5,424,096 A | 6/1995 | Anthony et al. | |
| 5,451,430 A | 9/1995 | Anthony et al. | |
| 5,464,665 A | 11/1995 | Anthony et al. | |
| 5,551,277 A | 9/1996 | Anthony et al. | |
| 5,573,607 A | 11/1996 | Weaver | 148/437 |
| 5,573,985 A | 11/1996 | Weaver | 501/96 |
| 5,874,175 A | 2/1999 | Li | |
| 5,932,348 A | 8/1999 | Li | |

OTHER PUBLICATIONS

"Thin–Film Transistors for Video Applications", Credelle, T., 1988 International Display Research Conference, (1988).
"Laser Method for Synthesis and Processing of Continuous Diamond Films on Non–Diamond Substrates", Narayan, J., Science, vol. 252, Apr. 19, 1991.
"Current Research and Future Outlook of Japan", Suga, T., (1989).
"Status and Applications of Diamond and Diamond–Like Materials: An Emerging Technology", DTIC Report AD–A22 986, National Research Council. 1990.
"Physical Metallurgy of Steels", Physical Metallurgy, Cahn, R.W., New York, 1970.
"Diamond Metallization", 3rd International Symposium on Diamond Materials, Li, C., Hawaii, May 16–21, 1993.
"Ferrous Physical Metallurgy", Sinha, A.K., Butterworths, Boston, 1989.
"Optics Industry Report", Laser Focus World, Jan., 1993.
"Transitional Metal Carbides & Nitrides", Toth, L. E., Academic Press, New York 1971.
"Annealing Effect on the Resistivity of Polycrystalline Silicon Films Passivated with Plasma–Deposited Silicon–Nitride Films", Saito, Y., J. Appl. Phys. (63(4)), Feb. 15, 1988.
"Hydrogen Passivation of Polysilicon MOSFET's From a Plasma Nitride Source", Pollack et al., IEEE Electron Device Letters, vol. EDL–5, No. 11, Nov. 1984.
"Ferroelectric Liquid–Crystal Shutter Array with Poly–S; TPT Driver", 1988 International Display Research Conference, Okumura, F. 1988.
"Inversion Layer Mobility of MOSFET's Fabricated with NMOS Submicrometer Technology" Manchanda, L. IEEE Electron Device Letters, vol. EDL–5, No. 11, Nov., 1984.
"Joining Ceramics", Loehman, R., Ceramic Bulletin, vol. 67, No. 2, 1988.
"From Technology to the Science of Glass/Metal and Ceramic/Metal Sealing", Pask, J., Ceramic Bulletin, vol. 66, No. 11, 1987.
"Fanning the Hope for a Flat Diamond", Amato, I., Apr., 1991.
Ceramic Bulletin, vol. 68, No. 9, 1989, pp. 1592–1599.

* cited by examiner

CERAMIC COATING METHOD

REFERENCE TO RELATED APPLICATIONS

This application is a continuation-in-part of application Ser. No. 08/301,582 filed on Sep. 7, 1994 now U.S. Pat. No. 5,874,175, which is a continuation-in-part of application Ser. No. 08/123,877 filed on Sep. 23, 1993 and now U.S. Pat. No. 5,392,982, which is a continuation-in-part of each of application Ser. No. 07/804,287 filed Dec. 9, 1991 now abandoned, application Ser. No. 07/804,285 filed on Dec. 9, 1991 and now U.S. Pat. No. 5,248,079, and application Ser. No. 07/644,421 filed on Jan. 22, 1991 and now U.S. Pat. No. 5,230,924. Each of application Ser. Nos. 07/804,287 and 07/804,285 is a continuation-in-part of application Ser. No. 07/499,707 filed on Mar. 27, 1990 and now U.S. Pat. No. 5,161,728 which is a CIP of Ser. No. 07/277,666 filed Nov. 29, 1988, now U.S. Pat. No. 4,890,783. Application Ser. Nos. 07/499,707 and 07/644,421 are continuations-in-part of application Ser. No. 07/277,672 filed on Dec. 14, 1988 and now U.S. Pat. No. 5,000,986.

BACKGROUND OF THE INVENTION

1. Field

This invention relates to ceramic coating and bonding methods, and more particularly relates to fusion-formed, ceramic coating and bonding methods with uniform ceramic metallizing compositions and specially graded, microscopically substantially perfectly defect-free bonded regions to produce reproducibly strong and thermomechanically shock-resistant ceramic coatings or bonds.

"Ceramic" means not only the usual ceramics such as alumina, zirconia, beryllia, mullite, cordierite, silicon carbide; but also quartz, intermetallics, diamond, boron, graphite, carbon, silicon, and various other carbides, nitrides, aluminides, or borides, glasses, machinable glasses, Corning's Vision glass; but also the surface of many reactive metals such as aluminum, magnesium, chromium, silicon, titanium, or zirconium which always have oxides, nitrides, hydrides, or other compounds of reactions of the metal with the environment.

2. Prior Art

Various methods have been developed to coat ceramic or metal with, or to join metal to, ceramics. But none gives inexpensive, stable, strong, and temperature resistant products. Reliable ceramic coatings or joints are not commercially available worldwide at any cost, even for small joint sizes.

Under a well-coordinated intensive effort on ceramic-metal bonding, Japan has been the most successful country in the development and commercialization of products involving metal-ceramic bonds. They already have successfully: (1) used a ceramic turbocharger (NGK, Nissan), (2) produced an all ceramic swirl chamber for diesel engines (Mazda, NGK), and (3) prototyped a ceramic turbomolecular pump (Mitsubuishi and Japan Atomic Energy Research Institute). But according to Prof. T. Suga of the University of Tokyo in his 1989 review paper on the "Future Outlook in Japan" (Exhibit A), the practical useful temperature of the best Japanese ceramic joints to special "matching" metal alloys is only 600° C. Further, the bond strength decreases rapidly with temperature, because the reaction products in their bonded regions become weak and brittle under thermal stresses. They consider the improvement of the thermomechanical shock resistance of their brazed ceramic joints to be an urgent task.

The European effort, mainly in Germany and France, has been even less successful. Germany failed to reach their goal after the first ten-year (1974–1983) program and its follow-up in 1983–1986. Their present program (1985–1994) merely emphasizes on reproducible mechanical properties and component reliability. The US Department of Energy supports much of US ceramic joining R&D. It also had to renew annually the ceramic automotive program after 10-year, 50-million intensive work, mainly producing a specification for automatic ceramic-metal joints.

Each metal-ceramic joint or bond must be specially designed. The factors in joint design include metal and ceramic composition, joint failure modes, parts shapes and sizes, thermal and other demands. The requirements for the National Aero-Space Plane (NASP) is totally different from those of the diamond heat sinks or fusion reactors. A ceramic-metal bond designed for maximum mechanical strength is usually not the best for thermal conductances, which is critical in heat sinks. What is best for one application (e.g., for preventing rapid heating failures) may even be precisely the worst for another (e.g., for preventing severe quenching failures), as shown by the functional grading technique described in this application. On the NASP, for example, the best titanium-$Si_3N_4$ joint for the turbine subjected to rapid heating should not be used for the wings of the same plane subjected to possible ice quenching failures. A joining method for many conditions may not be the best for any application.

Different physical, chemical, and electrical metallizing or film-forming methods have been developed for metal-ceramic bonding. Each method has its unique advantages. Some, for example, are atomically precise. Others thoroughly clean the substrate surfaces for better adhesion. Some others result in crystalline epitaxy, which is necessary for semiconductor devices. Still others produce splat cooling and superfine grains, with resultant enhanced mechanical properties, for example, increased Young's modulus. Still others are done at low temperatures to avoid unwanted thermal effects. But none deal effectively with the many critical problem to be addressed in this invention.

Most ceramic-metal joints have bonding regions that are not microscopically perfect or 100% dense, severely damaging the joint mechanical strength and thermal or electrical conductivities. Sintered, solid-state formed, hot or cold pressed, diffusion bonded, or even liquid infiltrated bonding layers cannot be fully dense, no matter how high the vacuum, external pressure, or processing temperature. This is because trapped gases cannot be compressed to zero volume, particularly if they are sealed off by initial densifications. Evaporated, sputtered, plasma, and electrolytic or electroless deposits generally are packed plates. Packed particles can never be 100% dense. The maximum density in packed spheres is only about 74% for the idealized close-packed, face-centered or hexagonal packing structure. Ceramic metallizing with mixed W/Mo and Fe/Mn powders have voids and segregations initially already present in the coated layers. These defects, generally remain after high-temperature processing, because of contamination, inadequate melting and fluxing, and diffusion voids, and other chemical reactions. Repeated metallizing, sintering, nickeling, as suggested by, e.g., the U.S. Pat. No. 3,901,772, do not solve the basic problems.

Achieving full density in chemical vapor deposition (CVD) or physical vapor deposition (PVD) requires not only complete absence of dust, contamination, inclusion, and trapped gas, but also special ambient such as excellent vacuum, not gaseous ambient under atmospheric pressure.

Deposited films also require perfect cleaning and optimal nucleation and crystal growth. Nucleation and crystal growth is still not a science. The later, in particular, requires unknown but continuously varying growth rates and temperature profiles. After billions of dollars of CVD work (e.g., in electronics), defects in CVD films are still prevalent. Pores, for example, often reach up to 10 or 20% in even the most studied diamond films, according to a 1990 DTIC report referred to elsewhere. This is so regardless of whether high or low-pressure, high or low-temperature, plasma or laser enhanced or not, or the type of equipment, carrier gases or reactants used. Unless ultra-high vacuum is used, active metal bonding methods employing Ti, Zr, Nb, Cr, . . . always contains surface oxides, nitrides, carbides, which lead to pores or cracks (from mismatch between, e.g., oxide or metal) and refractory, non-wetted or non-bonded areas.

The metal powders used in the common ceramic metallizing processes are limited to 325 or 400 mesh sizes, or still tens of microns in diameters. Finer powders are costly, and generally surface contaminated. These fine mixed powders are always segregated, and cannot produce thin metallized layers one micron or 100 Angstroms (A) thick, nor with thickness accuracies of less than 1,000 or 100 A.

Hence, most ceramic-metal joints are not substantially perfectly bonded, not only microscopically but even macroscopically. By "macroscopically or microscopically substantially perfect wetting or bonding", it is meant that no defects are visible in the form of voids, cracks, excessive fluxes, non-wetted, or non-bonded areas under the microscope or on microphoto at 3–20 or 100–1,000 times magnification, respectively. Microphotos such as those in FIGS. 2 and 3 (at 1,000X magnification) of the Li's "Diamond Metallization" paper given in Ref. E mentioned elsewhere show microscopically perfect bonding with none of the defects mentioned above. These microphotos are available to the public since 1990 via the SDIO Final Report, Ref. 17, in the "Diamond Metallization" paper.

Many problems still exist with present ceramic metallizing, coating, and bonding methods. A serious problem is the instability and unreliability of even the best ceramic-metal bonds made in, e.g., Japan, as mentioned above. Another problem is the difficulty of achieving on the ceramic surface uniform metallized layers, or even coated layer of the metallizing powders.

Take, for example, the commonly used heavy metal processes, such as W-Yttria (W—$Y_2O_3$), W—Fe, or Mo—Mn. In these and many similar methods, segregation of the mixed metal powders takes place due to their differing specific gravities, shapes, sizes, porosities, and surface smoothness. These segregation occur at all times: during the mixing of the powders, storing of the powder suspensions, application of the suspensions, settling of the suspended powders in the applied coatings, and drying of the applied coatings. Further, these segregations occur so fast as to be practically uncontrollable, as will be shown shortly.

In general, spherical, heavy, large, smooth, and dense powders settle first and early in the binder or suspension medium. Upon settling, these powders tend to roll or move sidewise or downward toward the corners or boundaries faster and further than odd-shaped, light, small, rough, and porous powders of otherwise identical characteristics.

Take the W—$Y_2O_3$ mixed powders in an organic binder of nitrocellulose in butyl carbitol acetate with specific gravities of 19.3, 4.5, and 0.98, respectively. Such a suspension, even if perfectly mixed up by shaking, stirring, roller-milling, or otherwise, will immediately tend to segregate. More specifically, the initial settling acceleration due to gravitational minus buoyancy forces on W powders is 980.6X (19.3–0.98)/19.3=930.8 cm×cm/sec, while that of $Y_2O_3$ powders is only 767.0 cm×cm/sec.

In a mixing, storing, or carrying bottle 10 cm high and containing a perfectly mixed suspension of these mixed metallizing powders, the time for the W powders to completely settle out is only 147 ms (milliseconds), if uniform acceleration is assumed. At the tip of a paint brush having a suspension drop 0.3 cm in diameter, the complete settling time of these W powders is merely 25.4 ms, while on a horizontally painted or sprayed layer 0.1 cm thick, the same settling time is only 14.7 ms. In all these cases, the complete settling time for the $Y_2O_3$ powders is always the square root of 930.8/767.0=1.21, or 21% longer, as shown in the U.S. Pat. No. 4,890,783.

Assuming uniform accelerations, mixed powder segregations may be completed within 147 to 14.7 ms. Such short times indicate that the W—$Y_2O_3$ powder segregations are beyond human controls. Painted or sprayed mixed powder layers are thus always not uniform.

In metallizing onto a horizontal ceramic surface, most of the W powders immediately settle out. The first coated layers are therefore always very rich in W (melting point 3,410° C.), and correspondingly very poor in $Y_2O_3$. These first layers are too refractory for the preset metallizing temperature (up to about 1550° C.) to melt, so that the ceramic surfaces are not sufficiently metallized, or not at all. The last settling layers, on the other hand, are too rich in the fluxing $Y_2O_3$. Thus, the ceramic surfaces are improperly metallized, with bottom undermetallized layer and top glassy layer. The metallized bonding layer is either erratic, or very weak in strength and thermal or thermal shock resistance.

Hence, common W/Mo metallization on ceramics generally produces unreliable or uncontrollable results. The metallized surface often contain loose and unmetallized spots with high heavy refractory metal content, or non-wettable spots due to the high flux content. Even repeated metallization, brushings, and nickel or copper platings, as suggested in U.S. Pat. No. 3,910,772, do not solve the basic microstructural problem due to powder segregation. The entire process is costly, critical and involved, and yet non-uniform. The resultant ceramic-metal joints or ceramic coatings on metals are also weak, costly, nonreproducible, and usually not vacuum-tight, or temperature-resistant, e.g., less than 600° C. even in the best Japanese joints with superfine ceramics and "matching" high-nickel metals, as mentioned above.

Painting or spraying onto vertical or inclined surfaces results in additional segregations and gradations, and gives added poor uniformity, reproducibility, and bonding results. While only the effect of gravitational density segregation has been considered in some detail in the U.S. Pat. No. 4,890,783, the other segregation variables such as powder shape, size, porosity, and surface roughness are also important. This and other previous inventions achieve significant improvements never before possible. Still, absolute joint perfection is evidently impossible.

A second important problem with common joining processes is the lack of control, or even understanding, of dynamic mismatches of temperatures, coefficients of thermal expansion (CTE's), stresses, and strain profiles in the joint region, and their variations with time. Another aspect of this invention is therefore to describe such dynamic mismatch phenomena, and to specially tailor-grade the composition and/or physical property profiles of the joint region so that the maximum or critical transient mismatch stresses never exceed the local material strength at any point inside the joint region, at any time during the heating or cooling of such joints in processing or service.

A third problem results from our incomplete understanding of the required microstructural, chemical, and physical properties of the interfacial regions in the ceramic-metal joints.

These gravitational segregation, dynamic mismatch, and joint design problems have been described and preliminarily solved in the U.S. Pat. No. 4,890,783 and other patents. This invention is to continue to improve upon these previous solutions.

Accordingly, an object of this invention is to provide improved ceramic-metal joints and joining methods;

A further object of this invention is to provide improved ceramic metallizing methods for these joints;

A broad object of this invention is to minimize gravitational segregations of the components in the metallizing methods during or prior to the joining;

Another broad object of the invention is to functionally tailor-grade, both parallel to and normally of the thin bonding region, the composition and property profiles in the bonding regions to ensure that the maximum dynamic or transient stresses do not exceed the local material strengths at any point and time;

A further object of the invention is to provide a specially microengineered, highly wetting and perfectly bonded interfacial bonding layer of the optimum characteristics to achieve defect-free, tough, and very strong joints;

A still further object of the invention is to provide uniformly thin (1 micron, 1,000 A, or 100 A) bonding layers with controlled uniformity and thickness accurate to 100 or 10 A;

Another object of the invention is to flawlessly coat metals or ceramics with protective materials, particularly to produce tough, strong, thermochemically stable, and thermomechanically shock-resistant composites;

Another object of the invention is to provide improved method for making, and products of, diamond, silicon carbide, and other ceramic joints to metals;

Further objects and advantages of my invention will appears as the specification proceeds.

SUMMARY OF THE INVENTION

To these ends, the method of the present invention for making a microscopically perfectly wetted and bonded, void-free and crack-free, structural bond between a metal and a ceramic for practical uses above 600° C. comprises uniformly metallizing the ceramic; and increasing the ratio of the ceramic material strength to the dynamic and static mismatch stresses due to differential thermal expansions so that these mismatch stresses do not exceed the ceramic material strength at any point and time thereby preventing bond failures.

DESCRIPTION OF THE DRAWINGS

The invention and its further objects and features will be more clearly understood from the following detailed description taken in conjunction with the drawings in which.

DESCRIPTION OF THE PREFERRED EMBODIMENTS

Figure 1:
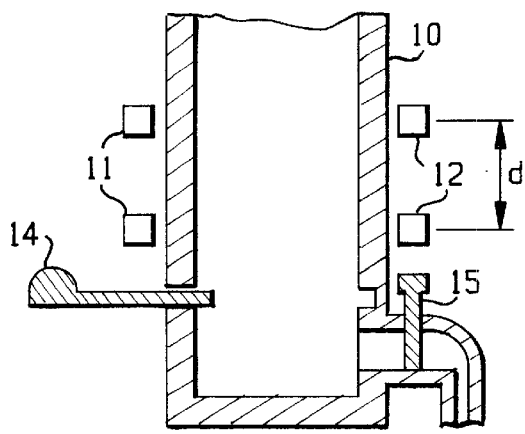
FIG. 1 shows a system for real-time monitoring of mixed settling powders.

With the above and such other object in view as may hereinafter more fully appear, the invention consists of the novel (structures, articles constructions and methods) constructions, combinations and arrangements of parts as will be more fully described in the accompanying specification and illustrated in the accompanying drawings, but it is to be understood that changes, variations, and modifications may be resorted to which fall within the scope of the invention as claimed without departing from the nature and spirit of the invention.

It will be understood that the specific embodiments described herein are merely illustrative of the general principles of the invention and that various modifications and equivalent substitutions are feasible without departing from the spirit and scope of the invention. That is, the invention is of general applicability for improving the quality of the ceramic-metal joints or joining methods, or coatings of ceramics on ceramics, or on metals. It is also evident that materials, structures, and methods other than those especially described can be combined and used to practice the invention.

The U.S. Pat. No. 4,890,783 and other patents of Li describe the gravitational segregation of mixed metallizing and/or brazing powders of different diameters and suspended in a common fluid (gas or liquid) suspension medium of a specific viscosity n of the suspension medium at the processing temperature for coating. Equations have been derived showing the relationship of the particle diameter $D_i$ (for the ith particle type), its density $d_i$, and viscosity n to the settling velocity and distance. Stokes in 1851 first considered the resistance R which a fluid medium of density $d_m$ and viscosity n offers to the movement of any spherical powder. His work enables the derivation of equations for the powder's acceleration, velocities, final velocity $v_f$, and a "velocity constant". The velocity constant, which characterizes the settling of the particle (of size $D_p$ and density $d_p$) in the suspension medium, is given as follows:

$$v_c = v_f/D^2 = (d_p - d_m) \, g/18 \, n$$

One can calculate the velocity constant and the settling behavior in water at 20° C. ($d_m$=1.0 and n=0.010) of various metal or nonmetal powders, with densities in g/cc in parentheses, as follows: W (19.35) 100,000, $Y_2O_3$ (5.01) 21,900, Fe (7.87) 37,400, Mo (10.2) 50,100, Mn (7.2) 33,800, $WO_3$ (7.16) 33,600, $Fe_2O_3$ (5.24) 23,100, $MoO_3$ (4.692) 20,100, and $MnO_2$ (5.026) 21,900.

For example, according to CRC Handbook of Chemistry and Physics, Ed. D. R. Lide, CRC Press, 1993, W (page 4–109), Mo (4-76), Cu (4–57),, $Bi_2O_3$ (4–44), $WO_3$ (4–109), CuO (4–57), $MoO_3$ (4–76) and diamond (12–79) have densities of 19.4, 10.2, 8.92, 8.9, 7.16, 6.4, 4.69, and 3.51, respectively. Hence, when mixed in a binder suspension, these particles settle out into layers in the sequence given, as shown in the U.S. Pat. No. 4,890,783. Diamond, being the lightest, therefore settles out last, or predominantly as the topmost layer over the other material layers.

Also, in the W—$Y_2O_3$ metallizing process, because the W powders are 3.9 (19.35/5.01) times heavier than $Y_2O_3$, the velocity constants $v_c$'s of the two components differ by a factor of 100,000/21,900=4.6 times. That is, for a given powder size D, the final constant settling velocity $v_f$ of W spheres is 4.6 times greater than that of $Y_2O_3$ spheres. As discussed above, this wide difference in velocities results in severe gravitational segregation and early depletion of W particles in the settling mixtures and, therefore, non-uniform poor metallizing results.

The closer the densities and velocity constants of the mixed powders, the less the gravitational segregation. Hence, the powders in the mixed oxide process $WO_3$—$Fe_2O_3$ are much less segregated and more uniform than the mixed metal particles, W—Fe. The $WO_3$—$Fe_2O_3$ process has density and velocity constant ratios of 1.366 and 1.455, versus 2.459 and 2.674, respectively, for the W—Fe process. Similarly, in the Mo—Mn process, replacing the metal powders by their respective oxides reduces the differences in the ratios of velocity constants and final velocities from 48.2% to only 9.0% and 19.2% to 4.2%, respectively. Powdered oxide or other compounds of W, Fe, Mo, and Mn are reduced during metallizing from their respective oxides to form the respective metal powders. These metal powders are smaller than the initial oxide powders. These smaller sizes further promote better homogenization and metallization results.

If we mix $Fe_2O_3$ and $WO_3$ spherical powders in the size (diameter D) ratio of the square root of the velocity constant ratios (33,600/23,100=1.455), i.e., 1.206, the final settling velocities of both these size-ratioed powders will be exactly the same. That is, by simply making the $Fe_2O_3$ powders 20.6% larger than the $WO_3$ powders, the mixed particles will finally settle in water at 20° C. at exactly the same velocity. This condition leads to metallizing uniformity due to the uniform composition of the finally deposited layers.

The final settling velocities of the two mixed powders, $v_s$'s, however, come only after some settling time, $t_s$, when a specific amount, Q, of the mixed powders has already settled out at differing velocities. From this settling time, $t_s$, for the specific combination of component powders, the settled amount Q, and the material use efficiency can be computed from the materials remaining after the settling time, $t_s$. The materials already settled before $t_s$ is the settled distances, $s_f$, multiplied by the initial material densities. The already settled materials are not lost, since they can be recirculated and reused in subsequent metallizing runs.

In this way, gravitational segregations between, for example, co-settling W and Fe, Mo and Mn, $WO_3$ and $Fe_2O_3$, or $MoO_3$ and $MnO_2$ powders, are minimized. Naturally, the smaller the percentage of velocity or useful powder size differences, the lower the material use efficiency on a particular mixed-powder combination. An engineering compromise must, therefore, be made.

The fluid suspension medium may be either a gaseous or liquid medium. The liquid may be water, alcohol, other inorganic or organic liquids of fairly constant viscosity at room temperature. A varying viscosity liquid may also be used, for example, a polymerizing organic substance containing a polymer and a hardener, a nitrocellulose in an evaporating solvent such as butyl carbitol acetate, or Duco cement diluted with rapidly evaporating acetone, to achieve rapidly increasing viscosity, n. The velocity constant of the settling powders is, as shown above, inversely proportional to this viscosity. Hence, in all these cases, the starting time for achieving nearly equal settling velocities is shortened by the increasing viscosity due to polymerization or solvent evaporation. With increasing viscosities, the absolute difference between the settling velocities (in centimeters per second) of the two mixed powders becomes less. Nearly equal-settling conditions are thus more easily achieved for the mixed powders. But the nearly equally settling, mixed powders must be quickly used before much further polymerization or evaporation takes place.

The above technique minimizes gravitational segregation through minimized settling differences of powders of differing densities. The technique achieves uniform chemical compositions in the different layers of settled metallizing powders. Absolute, 100% segregation control and coating uniformity is impossible, partly because there are other types of segregations besides size segregations due to gravity treated in the U.S. Pat. No. 4,890,783. Even different settled coating layers still slightly differ in chemical compositions. These differences are even more pronounced after the ceramic metallization, because the metallization reactions are diffusion controlled. Even with perfectly uniform settled powder compositions, the chemical compositions of resultant metallized layer, though substantially uniform, particularly in any plane parallel to the ceramic-metal bonding interface, also depends on the (diffusion) distance from the metal substrate surface.

In practice, we specify that the two settling velocities of the mixed particles are within a certain specified percentage, e.g., 20 or 10%, of each other.

By repeated experimentation or computer simulation, the best mixed-powder metallizing process for optimal combined metallizing uniformity and material use efficiency can be systematically determined. Based on these principles, method and equipment can be developed for controlling the turn-on time for starting to deposit the mixed powder at nearly equal final settling velocity into metallizing layers with the size-ratioed powders.

FIG. 1 shows such a system for real-time monitoring of the settling powders. The system determines the starting time for collecting the residual or still unsettled mixed powders for uses in metallization. This system has a vertical settling cylinder 10. Near the bottom of the cylinder 10, two pairs of light emitters 11 and detectors 12 are located at two different heights with emitters on one side and detectors on the opposite side of the cylinder. The two emitter/detector pairs sense the settling particles, as follows. The times for the powders to pass the top or bottom emitter/detector pair determine the powder size or type being monitored, while the times for the powder to transverse through the vertical distance d between the heights give their velocities. When the settling velocities of the two types (and sizes) of the powders are within a specified percentages, a sliding shuttle 14 is moved to catch on the shuttle the residual or unsettled mixed powder of nearly equal settling velocities. These equal-settling mixed powders in suspension are separated for immediate metallizing use while the already settled powders are drained through the valve 15 for subsequent reuse.

The above method of minimizing gravitational segregation is useful not only in ceramic metallizing, but also in painting, depositing, injecting, food preparation, or plasma spraying with multiple solid or liquid materials of differing densities suspended in a gas or liquid. In plasma spraying of mixed powders, one has to consider not only vertically downward gravitational segregation of the settling powders in a gas medium, but also the propulsive forces of the superheated, high-velocity plasma gas jets acting usually horizontally to propel and float or suspend the mixed solid powders or liquid droplets to reach the target spray areas with uniform mixed powder compositions. Apparently, the above technique for minimizing gravitational segregation through minimized settling differences can be used to handle more than two types of powders of differing densities.

Useful metallizing compositions include the commonly used W:Fe or Mo:Mn system containing 10 to 30 weight percent of Fe or Mn, or their derivatives $WO_3:Fe_2O_3$, $MoO_3:MnO_2$, or other non-oxide systems. From the atomic or molecular weights of the elements W, Mo, Fe, Mn, O, Cl, F, I, Br, . . . or radicals $NO_3$, $SO_4$, . . . , the weight percentage of the heavy metal W or Mo and the other braze and melting temperature-lowering metals such as Cu, Zn, Pb, Sn, Sb, Bi, Fe, Mn, Ag, Au, In, . . . used for the paste, suspension, or solution metallizing compositions can be readily determined. Generally, the same ratio of 10 to 40 weight percent of braze metal to the 90 to 60 percent of heavy metal is maintained in these compositions.

Another way to insure a substantially constant chemical composition consisting of two or more mixed metallizing powders having different densities and carried in a fluid suspension medium is to cause the two types of materials to come out of the suspension medium in a substantially constant chemical composition thereby ensuring uniformity and reproducibility of the metallizing results. For example, the two types of materials may be integrated into physically integral and inseparable forms, such as by alloying or coating the internal or external surface of one type of powders with the other to form integrated coated powders. Alloyed or coated with iron, W may form integral or inseparable W—Fe powders. Similarly, molybdenum may be alloyed or coated with manganese to form integral Mo—Mn powders that will not segregate.

Another method to minimize segregation of a single fluxing (e.g., MgO, $Y_2O_3$) or brazing (e.g., Cu, CuO, Zn, ZnO), co-metallizing (e.g., Mn or MnO2 with Mo or Fe or $Fe_2O_3$ with W) material is the use of an aqueous or other solution of the W and/or Mo compounds. Sodium molybdate or tungstate, for example, is soluble in water. So is $MoO_3$ or $WO_3$ in hot water. Here, the solution may also be the settling medium itself and the suspended powders are of a single type. This composition can hardly segregate. Solutions of compounds of Cu, Zn, Fe, Mo, . . . , with powders of W, Mo, $WO_3$, or $MoO_3$ achieve the same results.

Yet another method to minimize segregation of a metallizing and/or brazing composition is to sequentially deposit or co-deposit the various metallizing and/or brazing metals on a ceramic powder, such as diamond, carbon, alumina, zirconia, or silicon carbide. The depositing may be by chemical or physical methods such as vacuum evaporation, and sputtering, ion plating, electrolytic or electroless plating, and plasma spraying. The heated ceramic powders may also be fluidized in an atmosphere of the metal halides, organo-metallic compounds, or other suitable gaseous medium flowing in a suitable processing chamber. The processing chamber is heated to the metallizing temperature so that the resultant fluidized product is a specially pre-coated, but non-bonded or non-aggregating powders. These surface-metallized powders may later be bonded at lower temperatures by using, for example, an In—Sn or Pb—Sn low-temperature soldering process. Such a procedure is particularly suitable for mounting low-melting ceramics, glasses, or delicate electronic circuits. All of these components cannot be processed at the usual high metallizing temperatures.

To completely eliminate gravitational segregations, complete solution metallizing is the ideal process. Many molybdenum and tungsten compounds are soluble in water, alcohol, acid, or bases. $MoO_3$, for example, is soluble in hot or ammoniated water. Oxide, chloride, nitrate, sulfate, halogen, and other compounds of iron, manganese, nickel, antimony, lead, tin, copper, zinc, and bismuth are much more soluble than $MoO_3$. Mixtures of W/Mo and the other solutions may be compounded into proper compositions for ceramic metallization. The use of solutions of compounds, e.g., halides of nickel, lead, tin, zinc, and copper allows these metal compounds to be reduced in a hydrogen or nitrogen/hydrogen atmosphere, generally at the atmospheric pressure of about 760 mm mercury, to supply the braze metal. In a single processing step, then, complete metallizing, brazing, and bonding is possible.

One difficulty of metallizing some ceramics such as MACOR, Corning Glass's machinable glass ceramic, by the solution method is the relatively low, allowable metallizing temperature of about 950° C. The solubilities of the metallizing compounds are also restricting factors. Still, many potential metallizing compounds are soluble or at least partly soluble. Zinc chloride and sodium molybdate, for example, are soluble up to 432 and 65 grams, respectively, per 100 cc of cold water. The solution is often filtered to remove solid particles contained therein.

Useful W/Mo-based metallizing compounds include: X (X=W or Mo), $XO_3$, $Na_2XO_4$, $K_2XO_4$, $Li_2XO_4$ and XH ($H=F_2$, $Br_2$, $Cl_2$, and $I_2$). Useful braze metal compounds include: many $YNO_3$, YZ (Y=Cu, Ag, Au, Zn, In, Fe, Ni, Mn, Ga, Sn, Pb, Cd, Tl, . . . , and Z=F, Br, Cl, and I). Many of these compounds are soluble in water, alcohol, or other organic or inorganic solvents and can, therefore, be used to prepare the metallizing solutions. Knowing the elemental atomic weights, one can readily compute the weight of metallizing W or Mo or braze metal in each gram of these chemical compounds.

Another important consideration in making dissimilar materials joints relates to thermal mismatch stresses and strains. In any ceramic-metal joints, or for that matter, any joining of portions of two dissimilar or similar materials, or even in a single-phase homogeneous material, the matching or mismatch in CTE's of their thermomechanical characteristics of the joined portions in general, and thermal expansion coefficients in particular, is extremely important. From the mismatch of their thermal expansions, thermal stresses result.

Mismatches in other thermomechanical characteristics also result in other thermomechanical mismatch stresses and strains. The magnitude of these mismatch stresses and strains determines the failure probability of the joint. Thermally generated mismatch stresses and strains are especially critical factors in dissimilar materials joints. In metal-ceramic joints, differences in coefficients of thermal expansion (CTE's) between the metal and the ceramic produce thermal-mismatch stresses and strains. These mismatch stresses and strains must be carefully controlled.

According to Hagy and Ritland's paper on "Viscosity Flow in Glass-to-Metal Seals," J. Amer. Ceram. Soc., Vol. 40, pp. 58–62, 1957, the CTE mismatch differentials of within 100 ppm (parts per million) are considered as allowable. However, such CTE mismatches relate to only the static, or thermal equilibrium, case. They do not truly represent dynamic or transient conditions when the joint is being heated or cooled. Yet such transient or dynamic conditions always exist during the manufacture or service of the joint.

An important problem with common joining processes is the understanding and control, over a period of cooling time, of dynamic mismatches in temperatures, CTE's, and thermal strain and stress profiles and gradients in the joint region. The U.S. Pat. No. 4,890,783 describes such dynamic mismatch phenomena and proposes special, laterally graded composition and/or physical property profiles of the joint region.

In some detail, the U.S. Pat. No. 4,890,783 patent provides computed mismatches in CTE's, stresses, and strains for, for example, a 5.08-cm diameter, cylindrical end-to-end steel-Macor joint at the cylindrical axes (where maximum dynamic mismatch stress occurs), for different times t=0 to 41,800 s after cooling from the brazing temperature of 950° C. to near room temperature at 20° C. The dynamic mismatches in thermal expansion coefficients, and the resultant thermal mismatch strains and stresses strongly depend on the joint materials, geometries, sizes, physical and surface properties, and heating or cooling conditions. A maximum of temperature differential of 775° C. occurs after cooling for t=1,000 s. The computed dynamic or transient mismatch strain reaches a maximum of about 0.0123 at t=1,000 s. Such a high strain, if not relieved or reduced, would exceed the yield point of the steel, which is joined to the even more rigid Macor.

The computed effective or dynamic CTE mismatch is more than two to five times greater than the corresponding mismatches for the static or equilibrium case, for cooling times of 10 s to 6,000 s. This ratio of dynamic CTE to the static CTE reaches a maximum of 5.3 at t=75 s. Also, the maximum computed dynamic CTE mismatch is about 29.6 $10^{-6}$ $C.^{-1}$, at a cooling time of t=90 s. Such a high dynamic CTE mismatch is intolerable because, according to the Hagy and Ritland criterion of 100 ppm, the joint becomes unsafe after only 3.4° C. of cooling.

For the 5.08-cm steel-Macor rod joint cooling from 950° C. to 20° C., the maximum dynamic stress, compressive in the MACOR ceramic and tensile in the steel, exceeds 37.1 kg/mm$^2$, well above Macor's flexural strength of 10.5 kg/mm$^2$ or even its comprehensive strength of 35.2 kg/mm$^2$.

Because of these high dynamic mismatches in temperatures, CTE's, strains, and stresses, the inadequate mechanical strength and thermal resistance of most conventional metal-ceramic joints in general, and steel-Macor joints in particular, are not surprising. Also, dynamic mismatch stresses, not static ones, usually cause the brazed metal-ceramic joint to fracture, and most ceramic coatings to crack, peel, flake, or spall.

Measures must therefore be taken to reduce the dynamic mismatch stresses on the relatively weak ceramic so that the ceramic is no longer subjected to the high stresses. This reduction can be achieved by, e.g., absorbing a major portion of the dynamic mismatch stresses normally present in the ceramic through the use of a soft, yieldable metallic braze. These measures prevent the brazed joint failures from these dynamic mismatch stresses. The residual or actual mismatch stress between the two joined materials is the theoretical mismatch stress with a portion thereof absorbed in the metallized or brazed layer.

Figure 6:
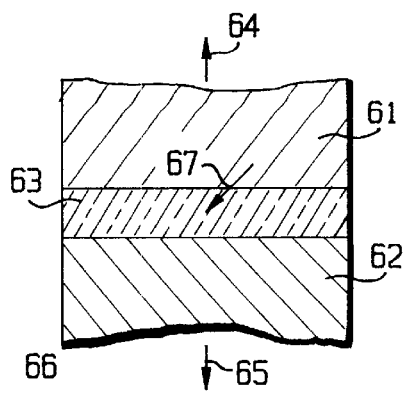
FIG. 6 shows a cooling method after metal-ceramic bonding to achieve controlled solidification and elemental segregation for overcoming dynamic mismatch stresses.
Figure 7:
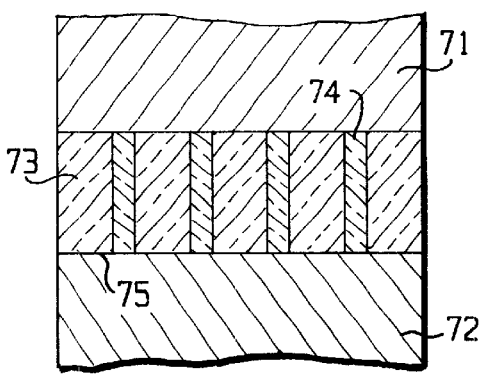
FIG. 7 shows a new method of overcoming mismatch stresses.

Specifically, this invention also describes the following methods, used singly or in combination, to minimize or neutralize these high mismatch stresses and strains:

1) A soft, yieldable metal layer used to braze the metallized ceramic to the metal, for absorbing within the braze layer a large or major portion of these mismatch stresses so that the relatively weak MACOR or other ceramic is no longer subjected to high stresses thereby preventing fractures;

2) Radial grading, rather than the common axial or longitudinal grading of the bonding interfacial region in thermal conductivity (or reciprocal of thermal resistivity), thermal expansion coefficient, and tensile strength of the braze metal, to ensure that the maximum residual mismatch stress, after absorption in the braze or shock-absorbing interfacial region, will not exceed the local material strength in the ceramic at any point and time;

3) A toughened and strengthened microengineered interfacial region between the ceramic and metallized layer to withstand thermomechanical shocks;

4) A new method to achieve flawless bonding regions;

5) Controlled cooling of the liquid braze layer to achieve radially outward solidification and elemental segregation for the desired patterns of radial grading properties (FIG. 6);

6) Using as the braze layer a plurality of strong columns of small lateral dimension L, embedded in a matrix of soft metal to minimize expansion differential, which is the product of L and the thermal expansion coefficient differential (FIG. 7);

7) Using elongated reinforced fibers or sheets locally placed normally of the potential fracture path and variably oriented along the local tensile fracturing stresses (FIG. 8); and 8) Combining radial grading with the conventional axial grading to change the thermal expansion coefficient of the braze layer from the ceramic side toward the metal side, to minimize direct mechanical interaction between the metal and ceramic members.

The first two methods are achieved by providing a novel composite metallic braze layer or disc consisting of a central copper core inside an outer copper alloy ring or washer made of, e.g., 70:30 Cartridge brass. This composite metallic disc joins together a ceramic body and a metal body. This disc is parallel to and forms part of the bonding interfacial region. The disc has a pure copper central core placed inside the opening of an outer 70:30 cartridge brass ring or washer. The CTE of pure copper is 16.5×10$^{-6°}$ $C.^{-1}$, while that of the cartridge brass is 19.9×10$^{-6°}$ $C.^{-1}$. Also, the Young's modulus of the brazing-annealed, dead-soft pure copper is much lower than that of the cartridge brass. The thermal conductivity of pure copper central core at 0° C. is 4.03 W/(m.K), while that of the outer cylindrical tube with 30% Zn in Cu is 1.14 (W/m.K).

The combination of high thermal conductivity and low CTE and Young's modulus in the central region of the joint achieves the required results. In a steel-ceramic joint, the maximum dynamic mismatches in temperatures, CTE's, and thermal strains or stresses occur at the axial centers of the interfacial region. A dead soft, brazing-annealed, pure copper therefore occupies the core region. Copper has a small Young's modulus, and a yield strength less than the fracture strength of the ceramic. It is easily deformable to absorb and relieve much of the dynamic mismatch thermal strains and stresses. Pure copper also has relatively low CTE to reduce these mismatch effects in the first place. In addition, the copper is a good thermal conductor, equalizing the temperature between the metal and ceramic to further minimize mismatch strains and stresses due to temperature differences.

On the other hand, the periphery of the braze disc is made of relatively more expansive but thermally lower-conducting 70:30 brass. At the peripheral region, the mismatch temperature differentials are relative small. The higher Young's modulus of the cartridge brass is even desirable at the peripheral region to enhance the joint rigidity.

This composite braze disc design will thus provide the radially graded profiles of braze composition, CTE, ductility, and thermal conductivity. All these graded profiles are favorable to minimize the critical dynamic-mismatch.

The composite braze metal discs can also be made by multiple printing, metallurgical cladding, mechanical press-forming of a sphere or disc inside a washer, or by sliced concentric metal tubes of graded compositions with a solid pure metal core.

Elemental interdiffusion during the braze manufacture, brazing operation, or special pre-brazing or post-brazing heat-treatments produce more diffused composition profiles in the braze discs and leads to more efficient lateral-grading results for a given transverse size of the bonded region. More description of the radially graded seals are given in my U.S. Pat. No. 4,890,783.

To practice the lateral grading invention, skilled persons can, of course, select other yieldable metals such as gold, silver, tin, lead, indium, zinc, iron, or nickel, and replace the copper-strengthening zinc with other metals. The resultant new alloys will, of course, be different in compositions, strengths, diffusivities, thermal conductivities, melting or softening points, and other properties.

Cu—Ag, Cu—Al, Cu—As, Cu—Bi, Cu—Ca, Cu—Cd, Cu—Fe, Cu—Li, Cu—Mg, Cu—Mn, Cu—Ni, Cu—P, Cu—Pd, Cu—Pt, Cu—S, Cu—Sb, Cu—Si, Cu—Sn, Cu—Te, Cu—Ti, and Cu—Zr are particularly useful to minimize dynamic mismatch stresses. Alloys of Ag, Al, Au, Bi, Cd, Co, Cr, Ge, Fe, Ir, Li, Mg, Mn, Mo, Ni, Pb, Pd, Pt, Rh, S, Sb, Si, Sn, Ta, Te, Ti, V, W, Zn, Zr, rather than Cu, are also useful. Higher-melting braze metals may also be used for high-temperature structural metal-ceramic joints.

The lateral grading technique produces liquid diffusion-graded metal-ceramic microjoints in parallel, while the conventional axial grading technique produces graded metal-ceramic microjoints in series. The optimum combination of both the lateral and the axial grading can be analyzed by computer simulation techniques. Even electrical analog techniques can be used to determine the optimum combination of parallel and series microjoints by arranging electrical resistors or capacitors in various parallel/series combinations.

All the above measures increase the ratio of the ceramic material strength to the dynamic and/or static mismatch stresses due to differential temperatures and thermal expansions. In this way, the mismatch stresses do not exceed the ceramic material strength at any point and time thereby preventing bond failures.

By properly controlling the cooling of a metal-ceramic joint, the desired lateral grading effect can also be achieved. For example, as shown in FIG. 6, after the joining of a metal cylinder or cylindrical plate 61 to a ceramic cylinder or cylindrical plate 62 of about the same diameter, the cylindrical surfaces are insulated thermally or cooled slowly relative to the free or unjoined ends. Heat is then extracted mainly axially at these ends 64 and 65. The center 67 of the bonding regions thus cools fast and solidifies first. The solidification therefore propagates radially outward.

According to the Ag—Cu phase diagram, in a Ag—Cu alloy braze disc, the first-freezing center portion has relatively pure Ag or Cu metal, if the original alloy composition contains less or more, respectively, than 28 weight percent of Cu. The subsequently solidifying and expanding cylinders in the resultant braze disc will be less and less pure in Ag or Cu, respectively. The last solidifying, outer cylindrical surface layer will be the Ag—Cu eutectic containing 28% (by weight) of Cu and 72% of Ag. Thus, the physical properties in the solidified braze disc are laterally graded by this solidification process. The central relatively pure metal portion of the bonding region will be softer and more thermally conductive than the peripheral eutectic region. By selecting a suitable alloying element or initial braze composition, the center can even also have a smaller thermal expansion coefficient than the peripheral eutectic, achieving maximum reduction in dynamic mismatch stresses. This controlled cooling method is particularly effective with large, flat joints when the ratio of diameter or lateral size is large relative to the length or thickness, thereby facilitating first cooling in the central portion.

FIG. 7 shows a joint between a metal 71 and a ceramic 72. Here, the braze layer 73 consists of a plurality of load-carrying, strong columns 74 (e.g., 70:30 Cartridge brass) embedded in a relatively soft matrix 75 of pure copper. Since the individual strong, load-carrying columns 74 have minimal lateral dimensions (a few millimeters or less), the thermal mismatch expansion strains and stresses are small.

Figure 8:
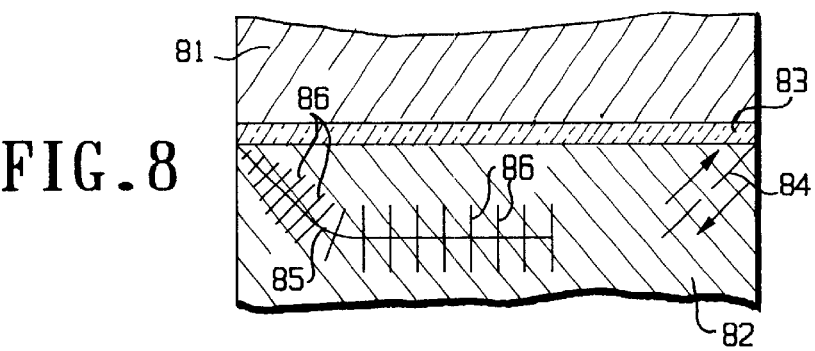
FIG. 8 shows another composite structure involving reinforcing fibers strategically positioned and oriented to overcome interfacial surface failures in the ceramic.

FIG. 8 shows the usual failure patterns in a metal (81)-ceramic (82) joint, or coating of ceramic on metal, due to mismatches that result in debonding, cracking, blistering, peeling, and spalling. As shown, the mismatch stresses are tensile in the metal 81 but compressive in the ceramic 82. The compressive stress induces in the ceramic a shear force which is maximum at the 45° plane 84 (see the right side of the figure). Therefore, the crack originates at the peripheral surface between the metal (including braze 83) and ceramic 82, but levels to the horizontal. The crack is inclined at 45° to the horizontal. To prevent these failures, elongated reinforcing members 86, such as strengthening carbon fibers or weaved sheets 86, are placed in the $Al_2O_3$ ceramic 82 in varying directions locally normally of the potential crack path, to best overcome the tensile mismatch stresses along the fracture path 85. In the left side of FIG. 8, the directions of the elongated reinforcing fibers thus change from 45° at the metal-ceramic interface to nearly vertical deep inside the ceramic 82.

Another new functional grading method to overcome dynamic stresses is to grade the composition, and therefore the thermal expansion coefficient and other physical properties of the ceramic such that the local composition gradient is roughly proportional to the local temperature gradient. There are four cases to be considered for this functional grading:

1. Maximum critical dynamic stresses occur when the ambient-exposed surface is rapidly heated with a constant ambient temperature heating, such as by inserting a ceramic-metal bond into a constant-temperature environment;

2. Maximum critical dynamic stresses occur when the outer surface is rapidly heated with a fixed quantity of heat, such as by high-intensity, constant-power pulsed laser or electron beam heating;

3. Maximum critical dynamic stresses occur when the outer surface is rapidly cooled with a constant ambient temperature bath, such as when the ceramic-bond joint is rapidly quenched in, e.g., air or water of constant temperature; and 4. Maximum critical dynamic stresses occur when the surface is rapidly cooled by taking away a fixed quantity of heat, such as applying a fixed quantity of water for rapid evaporation and heat removal.

In the thermal or equivalent material diffusion art, cases 1 and 3 are "infinite source" diffusions and have error function complement (erfc) solutions, while cases 2 and 4 are "constant-source" diffusions and have exponential function for their solutions. To overcome dynamic mismatch stresses due to transient thermal heating, the material compositions is functionally graded as to the major alloying element or elements, decreasing the thermal expansion coefficient or increasing the strength in proportion to their content such that the surface composition is also either error-function complementally graded or exponentially graded in the proper direction, respectively for cases 1 and 3, or 2 and 4. For cases 1 and 2 where heat is applied, the major element or elements controlling the thermal expansion coefficient are added to in-diffuse. For cases 3 and 4 requiring outdiffusion, a gettering material is used to get or remove the major elements from the surface so that the major controlling elements are subtracted or out-diffused with a getter material. For infinite material sources, constant-concentration ambient such as unlimited supply of gaseous, liquid, or solid diffusing material is used. For constant material sources, a limited or fixed quantity of diffusing material is employed.

After the surface diffusion or outdiffusion, with a constant or infinite source, the resultant surface composition profile or critical physical property profile will be similarly shaped (i.e., exponentially or erfc graded) like the anticipated maximum critical transient temperature profile. The directions of the thermal and composition profiles must be the same so that maximum temperature or composition (gradient) must occur at the same ceramic surface. This condition insures that the ceramic-metal joint can best withstand the transient thermal stresses due to the particular type of actual service transient heating or cooling.

The functional grading methods of overcoming dynamic mismatch stresses are not only useful for dissimilar material joints, but for even a single-phase material subjected to critical thermal surface profiles, such as when a carbon-carbon composite is rapidly heated by high-intensity laser pulses, or is rapidly surface quenched when hot.

If all these methods are still insufficient to prevent dynamic thermal mismatch failures, the conventional axial elemental grading or sudden composition changes may be added. One method consists of providing a disc of low-expansive metals such as Sylvania #4, Dumet, 50% nickel alloy, chrome-iron, stainless, platinum, Sealmet, and titanium placed between he steel and the copper braze. In this way, the ceramic such as MACOR is mechanically isolated from the highly expansive steel. The desired functional graded, elemental profiling can also be achieved through controlled diffusion and braze composition.

The computation of the dynamic mismatch stresses also provides a new, non-destructive testing (NDT) procedure. Stresses are stresses no matter how they originate. Stresses due to externally applied loads, internal residual stresses, phase transition-induced stresses, thermal mismatch stresses, and their combinations all cause the weaker ceramic to fail, precisely when the combined stresses exceed certain fracture strength of the ceramic. This failure always occurs at the moment of maximum dynamic mismatch stresses between the metal and ceramic, regardless of the proportions of the different types of stresses.

Qualitatively, the higher the allowable air or water quench temperature or severity, the higher the actual dynamic-mismatch stress and joint strength. There is even a calculable maximum "mechanically equivalent stress" produced by each quench treatment. A new, practically non-destructive test (NDT) for brazed ceramic-metal joints is now available, as shown below.

Under standardized cooling or quenching conditions, such as rapid (e.g. within 0.5 second) 20° C. air cooling or ice water quenching, there is a one-to-one correspondence between the joint strength (at, e.g., 20° C.) and the allowable initial cooling or quenching temperature. This temperature can be a direct measure of the joint strength for a specific joint configuration (e.g., cylindrical, end-to-end) and size (e.g., 5.08 cm in diameter). Preselected quenching and mechanical testing results will provide a useful date table correlating the quenching temperature and/or severity with the actual joint flexure strength for use in the NDT testing. This new test only destroys joints that fail mechanically, and yet is safe for all other joints. Hence, it is non-destructive.

Standard tensile or flexure tests are often difficult for metal-ceramic joints because of the critical jigging, loading, and sample alignment requirements. Actual metal-ceramic joints often also have complex geometries, and special material, size, composition, and property profile combinations. All these conditions make the standard mechanical test results difficult to reproduce and extrapolate to actual service conditions, or to determine if valid specifications have been met.

Yet, a controlled cooling or quenching test is simple and fast. It can be applied to a joint of any practical shape and size. There are no errors due to sample jigging, loading, and aligning. Nor are there any unknown joint damages due to handling prior to or during the actual testing. The results are often more relevant and immediately useful without extrapolations as to sizes, shapes, joint configurations, and thermal shock environments. In addition, the test is non-destructive if the specimen meets the specification. It is particularly useful and cost-effective for the following cases:

1. Joints of complex geometries and shapes.
2. Too large or small samples for existing testing machines.
3. Joints of combinations of materials with widely different hardnesses or other mechanical properties.
4. Joints that fail under dynamic cooling or heating conditions, which are difficult to duplicate on standard testing machines.
5. Joints of delicate parts which are hard to jig, align, or load. For example, it would be not only very costly but difficult to develop the necessary equipment and procedure for determining the bond strength of an irregular diamond crystal bonded onto a copper substrate for electronic heat sink applications.
6. Peeling, spalling, microcracking, and adherence to substrates of thin films.

In addition to achieve metallizing uniformity and minimal mismatch stresses, it is also important to microengnieer, or to design on a microscopic level, the chemical compositions, microstructures, and mechanical properties of the bonding interfacial regions between the ceramic and metallized layer. Merely perfecting the interfaces surfaces alone, as is commonly done, is not enough to produce strong and reliable joints for withstanding the unavoidable, severe mismatches stresses and strains as shown above.

For extremely shock-resistant joints or metallized layers, it is absolutely necessary to have a carefully microengineered interfacial layer between the ceramic and the metallized layer. This layer is designed to absorb the major portion of the always present mismatch stresses and strains. Many of the improved ceramic metallizing processes typically last 20 minutes and involve liquid-forming layers containing, directly or indirectly, W/Mo-based compounds such as $MoO_3$, which melts at 801° C. or $WO_3$, which melts at about 1,550° C. These melting points can be further reduced by alloying with compounds of the braze metals such as CuO, SnO, $Ag_2O$, $Sb_2O_3$, $Bi_2O_3$, ZnO or PbO. The reduced metal becomes molten, to freeze as the dead-soft annealed braze metal.

Liquid diffusion is rapid with a fairly constant diffusion coefficient $D_1=10^{-4}$ to $10^{-5}$ cm$^2$/sec. Processing for t=20 minutes gives a diffusion length of up to the square root of $D_1 \times t=0.35$ to 0.11 cm. The liquid diffusion during the ceramic metallization also forms wide diffused interfacial layer with graded and thermochemically stable composition, microstructures, and mechanical properties in a direction normally of the bonding plane. Such graded features are highly shock-absorbing.

In contrast, most conventional bonding or coating processes involve only solid-state diffusion. Solid diffusion is slow with diffusion coefficient $D_s=10^{-10}$ to $10^{-20}$ cm$^2$/sec. Even for the same processing or diffusion time t, which these processes do not have, the diffusion length is only 3.2 microns to 3.2 Å, or several orders of magnitude shorter than that in my liquid diffusion case. The mismatch stress gradient is thus proportionately steeper.

Liquid diffusion for 20 minutes produces a stabilizing effect and pre-aging or burning-in results, which are particularly important in the electrical art. Such effect and results would require about 19 years for solid diffusion results even at moderately high service temperatures such as 500° C. Liquid diffusion even for only 1, 3, or 5 minutes still provides a liquid diffusion length of 0.24, 0.42 or 0.55 mm, respectively. These diffusion lengths are sufficient for most cases.

Plasma spraying does involve liquid droplets in rapid transit. These extremely high-temperature droplets impact the substrate at very high velocities resulting in splat cooling with millisecond liquid dwell times. The resultant diffusion length is thus also over three orders of magnitude shorter than with the improved metallizing or metallizing-brazing method. Splat cooling gives very fine grains with high elastic moduli which actually increase the mismatch stresses. The extreme mismatch stress gradient (stress divided by diffusion length) makes the ceramic-metal bonds fragile. Also, the fine superheated liquid particles form refractory oxides, nitrides, or other surface layers during transit preventing perfect bonding between the particles themselves. Laser, electron, and some other energetic beam enhanced coating processes also give splat cooling and solid-diffusion conditions.

Without any external pressure on the ceramic to force the joining members together, the W/Mo metallizing and bonding processes described above perfectly join various ceramics to metals, often with pure copper brazes. A typical metallizing process comprises using a mixture of metallizing composition such as $WO_3$—$Fe_2O_3$ or $MoO_2$—$MnO_2$ in suspension or paste form and applied onto the ceramic, heating for 5 to 25 (preferably about 10) minutes the coated ceramic to about 800–1,450° C. (preferably 900–1,200° C. in most cases), with no pressure on the ceramic. The high metallizing temperature ensures thermochemical stability, reliability, and long life of the ceramic-metal bonds. The ratio of heavy metal W or Mo to Fe or Mn after reduction from the compounds is generally between 9:1 to 6:4. This metallizing may be followed by, or simultaneously done with, brazing. In the later case, a single-step metallizing/bonding results.

A neutral or reducing atmosphere, such as hydrogen or forming gases with 10 to 40 volume percent of hydrogen and 90 to 60 volume percent of nitrogen, is the desirable metallizing atmosphere. The metallizing environment may comprise, contains mainly of, or even consist essentially of, a hydrogen-containing gas, carbon-containing gas (particularly for diamond or related carbon), or a mixture thereof, usually at the atmospheric pressure of about 760 mm mercury. The hydrocarbon gas may be methane or propane.

Different compositions other than the usual mixed W—Fe or Mo—Mn mixed powders may also be used. For example, metal powders in the form of oxides, carbonates, nitrates, chlorides, fluorides, iodides, bromides, or other compounds of W, Mo, Cu, Ag, Au, Ni, Bi, Sn, Pb, Sb, In, . . . may be employed, generally in amounts from 10–90 by weight percent of the equivalent refractory W or Mo metal.

W or Mo is even not always necessary if active metals such as Ti and Zr are used to bond the ceramics. But the many other inventions of this application still apply, such as the methods for reducing dynamic mismatch stresses, sealing ceramic surface defects, functional grading, toughening and strengthening ceramic surface regions through microcomposite forming (with hard reinforcing particulates, roots, branches, networks), lateral grading, large-area joining, eutectic joining, single-metal metallizing/bonding, and the like.

W or Mo may not be necessary for other reasons. For example, in joining carbon (graphite, diamond) to iron alloys (steels, stainless steels, alloy steels), a single-step eutectic metallizing/brazing method may be desirable. This involves contacting carbon directly with steel, and heating the assembly to a temperature of from 1080–1350° C. Pure iron and carbon form a eutectic at 1154° C. at 4.3% by weight. of carbon. But common steels contains other elements such as Mn, Si, S, P, Al, Cr, Ni, . . . . All these elements lower the eutectic temperature and shift the eutectic carbon composition. Many of these elements themselves are carbide or eutectic formers with carbon. Hence, useful bonding with common carbon steels occur even at about 1050° C. Generally, the higher the bonding temperature, the better the bond strength and thermal shock resistance.

Iron and carbon forms a eutectic composed of iron and iron carbide $Fe_3C$. This eutectic microscopically substantially perfectly wets (wetting angle less than 5° or even 0°) and bonds carbon-based ceramics. Similarly, C and Ti form two carbides TiC and $Ti_2C$. Other metals such as those listed below also form carbides. The intermetallic compounds formed in ternary systems such as C—Ti—Pt, C—Ti—Au, Ti—Pt—Au, Ti—Pt—Cu, . . . are even more complex.

Graphite, carbon, or diamond surface may be first coated with a layer of the W/Mo-based material prior to the single-step metallizing/bonding process. The bonded carbon-steel joint may be water or ice water quenched while hot in the austenizing temperature range of, e.g., 900° C. Here, advantage is taken of the high thermal shock resistance of the new ceramic-metal joints to achieve full hardening and high strength and hardness of steel.

Using the same C—Fe eutectic brazing principle, other carbon-metal bonding methods are possible, according to T. B. Massalski's Binary Alloy Phase Diagrams, ASM, 1986, carbon also forms eutectics with: Au:3/1050 (namely, Au with 3 weight percent of carbon forms eutectic at 1050° C.), B:1.5/2075, Co:2.68/1321, Cr:3.2/1400, Hf:0.2/2250, Ir:1.6/2296, La:2.2/806, Li:2/165, Mn:1.3/1215, Mo:3/2205, Nb:7.5/2339, Ni:0.6/1326, Os:1.32/2732, Pd:2.8/1504, Pt:1.2/1705, Re:1.3/2486, Rh:2.1/1694, Ru:1.8/1924, Si:0.5/1404, Ta:2/2825, Th:0.5/1720, Ti:0.5/1648, U:0.1/1119, V:4/1650, W:1.9/2715, and Zr:0.4/1823. Instead of binary eutictic systems such as C—Fe systems shown above, ternary eutectics with multiple eutectic or carbide-forming elements selected from the above list are also possible.

The metallizing temperatures and times depend on factors including, e.g., unwanted chemical reactions. In graphite-aluminum composites, the metallizing temperature should not exceed about 750° C. to prevent carbide formations. A carburizing atmosphere, such as one containing $CH_4$ or propane, may be useful to prevent too much loss of carbon in the joining of carbon, diamond, or carbon-carbon composite. Diamond metallizing time may be only one minute to minimize graphitization at high temperatures.

Useful relatively low-melting soft and yieldable braze metals for this invention include pure copper (with melting point 1083° C.), silver (961.9° C.), gold (1064.4° C.), tin (232.0° C.), zinc (419.6° C.), lead (327.5° C.), antimony (630.5° C.), cadmium (320.9° C.), aluminum (660.4° C.), magnesium (648.8° C.), gallium (29.8° C.), indium (156.4° C.), thallium (303.5° C.), bismuth (271.3° C.) . . . , and their alloys. Higher-melting metals such as beryllium, chromium, cobalt, hafnium, iridium; iron, manganese, nickel, niobium, osmium; palladium, platinum, protactinium, rhenium, rhodium; ruthenium, samarium, scandium, silicon, tantalum; thorium, titanium, uranium, vanadium, yttrium, zirconium, and their alloys, allow the practical operating temperatures of the joints to be raised to within 50–150° C. of the respective melting points of 1278, 1857, 1495, 2227, 2410; 1535, 1244, 1455, 2468, 2700; 1554, 1772, 3000, 3180, 1966; 2310, 1300, 1541, 1430, 2996; 1800, 1660, 1130, 1890, 1522, and 1852 degrees Centigrade, respectively.

When molybdenum is used as the metallizing layer together with a braze metal such as osmium, rhenium, platinum, protactinium, rhenium, and tantalum braze layer, the lower-melting molybdenum, i.e., at 2810° C., rather than that of the braze layer, generally limits the useful temperature of the joint. In this new method, the Mo forms oxide which metallizes the ceramic while also provides itself as the substrate or alloys with the substrate or braze to form a ceramic-Mo or ceramic-Mo/braze-substrate bonded ceramic structure, respectively. Similarly, when tungsten (melting point 3410° C.) is used as both the metallized and brazed layer for more refractory ceramic materials such as carbon-based materials (melting point 3650° C.) to form a ceramic-W or ceramic-W/braze-substrate bonded ceramic structure, the lower-melting tungsten dominates as to the practical use temperature of the joint or coating. A variety of new, W/Mo metallized plates, fibers or particulates of, e.g., SiC, $Si_3N_4$, $Al_2O_3$, $ZrO_2$, mullite, cordierite, diamond, glass, quartz, and other ceramics can thus be produced that can be used as reinforcement in composites for temperatures over 1,500, 2,000, 2,500, 3,000° C., or higher.

Chemical reactions between the matrix and reinforcement often are serious problems in composites. In graphite-aluminum composites, for example, the graphite reinforcement reacts with matrix aluminum to form brittle aluminum carbide, particularly at service temperatures over about 800° C. The graphite-aluminum interfacial reactions is intolerable. High-melting metals, such as W or Mo, applied by use of the method of the above paragraph, can provide the metallized/brazed layers. These layers also serve as diffusion barriers on the graphite to slow down the elemental diffusion rates and, therefore, graphite-matrix interfacial reactions.

Elemental diffusion rates are functions of the ratio of the operating temperature to the absolute melting temperature. At the same operating temperature of, e.g., 550° C., this ratio for aluminum directly contacting graphite is $(550+273.1)/(660.4+273.1)=0.882$. With nickel braze on the graphite fibers according to the invention, the interfacial reaction is now between nickel and graphite, and the same ratio is reduced to $823.1/(1455+273.1)=0.476$. When the graphite fibers are metallized with Mo or W, the same ratios are further reduced to 0.267 or 0.223, respectively. With a wide variety of available metallizing alloys (e.g., W—Fe, Mo—Mn, . . . ) and coated layers on ceramic reinforcing fibers and particulates, these ratios can be selectively chosen to be less than, e.g., 0.6, 0.5, 0.4, 0.3, 0.22, or even less. The matrix-reinforcement interfacial chemical reactions are thereby reduced, while the weakening of composite strength is minimized and embrittlement of reinforcement or destruction of composite avoided.

Thus, interfacial chemical reactivity between the ceramic reinforcement and the metal matrix can be suppressed or totally eliminated by coating the metallized/brazed layer with chromium, nickel, aluminum, platinum, or other precious metals. Chromium, aluminum, and their alloys form adherent, dense oxides that resist further oxygen penetration to, e.g., the underneath graphite fibers. These specially metallized/coated graphite or carbon fibers are thermochemically stable in oxygen or other oxidizing atmospheres.

Ceramics already bonded with the new W/Mo-based metallizing methods include: diamond, alumina, zirconia, silicon carbide, beryllia, yttria, graphite, quartz, silicon, mullite, cordierite, Corning's MACOR and Vision glass, piezoelectric ceramics, graphite-aluminum composites, carbon-carbon composites, and 123 high-temperature superconductors. Useful structural metals for the joints include copper, nickel, stainless steel, high-nickel or cobalt iron alloys, or even highly "mismatched" ordinary cold-rolled SAE 1010 carbon steel. Even with the high "mismatch" between ceramic (e.g., $Al_2O_3$ or $ZrO_2$) and carbon steel, structural joints brazed with pure copper can be repeatedly thermal cycled without fractures between 980° C. (i.e., about 100° C. below the melting point of copper braze) and ice water followed by mechanical shocks including 8 to 10-foot drop tests onto carpeted, wood, or even marble floors.

Similarly, Poco graphite AXF-5Q to SAE 1010 carbon steel rods, ¼" in diameters and joined end-to-end, are almost mechanically indestructible even when heavily pounded with a 12-oz hammer. These joints also are resistant to rapid quench from 800° C. to 0° C. in ice water and severe mechanical shocks. Carbon-carbon composite with carbon steel joints yield comparable results. Joints of diamond to carbon steel can also withstand 850° C. quenching shocks.

These results show that:

1) With the improved W/Mo processes, low-cost "mismatched" (i.e., having coefficients of thermal expansion differing by over 40–100%) ceramic/metal, carbon-metal, ceramic-ceramic, or ceramic-graphite joints can be made;

2) These joints can be mechanically strong and thermally shock resistant. The bonding region can even be stronger than the ceramic;

3) Hence, the bonding processes, being ceramic material-limited, need no further improvement for these particular material combinations and thermal shock requirements;

4) These joints are, after bonding and thermomechanical shocks, free of pores, cracks, inclusions, inhomogeneities, and other defects at which fractures originate. Each of the shocks would multiply the number of defects exponentially and have failed the joints. These joints, including particularly the metallized layers, thus compare favorably with, e.g., certain ceramic-metal joints or ceramic materials developed at great cost, as reported in the literature;

5) These improved joints can have functionally graded compositions and physical properties to best withstand dynamic mismatch stresses; and 6) The improved or modified metallizing/brazing processes have achieved better bonding results than other methods including CVD, PVD, active metal process, hot or cold pressing, sintering, solid-state bonding, diffusion bonding, and infiltration.

If needed, surface plating or coating on the improved metal joints with various ceramics (including diamond, SiC, $Al_2O_3$, $ZrO_2$) may make the joints resistant to corrosion, erosion, oxidation, or surface reactions. Special metal-plated or coated ceramics can be made biocompatible for uses as implanted bones, teeth, or organs.

With diluted metallizing solutions, the new joints may use only thin layers of tungsten/molybdenum; and contain no other strategic and precious metals such as nickel, cobalt, chromium, gold, silver, platinum, osmium, and the like. The metallized layer provides a solid foundation or prime coat which adherently bonds to the ceramic. Upon this metallized layer, tenacious, protective metal or other ceramic layers can be brazed or formed which resist spalling, peeling, and thermomechanical shocks. The control of metal-metal interfacial bond strength has been well-known for hundreds of years. Improved corrosion, wear, or frictional properties on these coatings are also possible by suitable selection of the coating materials.

A solid lubricant system may, e.g., be made comprising graphite, talc, or $MoS_2$, titanium nitride, or silicon nitride powders chemically bonded in copper, bronze, nickel, steel, or cast iron. Also, carbon-carbon composites with improved strength and resistance to oxidation, thermomechanical cycling, and moisture penetration. Advanced chemically bonded intermetallic compounds of titanium or hafnium carbide, and titanium or nickel aluminides, are also made available. The same W/Mo-based metallizing compositions are even useful as almost universal high-temperature adhesives or sealants for many ceramics.

As shown above, ceramic coatings on metal or ceramic-metal bonds can be made even only with the metallizing molybdenum and/or tungsten, alone, without any braze metal layer. The useful operating temperature of the resultant products is then limited only by the high melting point of the refractory metallized layer for uses at temperatures over 2,000° C. or 3,000° C.

The microscopically flawless and defect-free quality of these ceramic-metal joints or metallized layers on ceramics, metals, or graphite, or metal-ceramic joints are particularly important for tough, fatigue-resistant, protective, easily wettable, and thermochemically stable coatings on ceramics, metals, graphite, or metal-ceramic joints. A metallized or coated graphite fiber, for example, cannot tolerate a single pinhole or microcrack that allows oxygen or moisture to penetrate and to destroy the fiber. Ceramic coatings on metals also cannot have defects when exposed to chemically reactive, high-intensity ion, plasma, or laser beams, high temperature, nuclear or plasma radiation, or other extreme environments. High-melting precious metals such as Pt, Os, and Pd, or oxidation-resistant metals such as Cr, Al, and Ni are therefore beneficially applied onto the metallized layer, or be formed simultaneously with a metallizing-brazing composition in a single-step metallizing-coating process. Once the ceramic is properly metallized, less protective metals such as gold, copper, magnesium, titanium, or zirconium may be applied onto, formed simultaneously with, the metallizing layer, followed by coating by electrolytic, electroless, or spraying methods, of the more protective, above-mentioned oxidation resistant metals for oxidation protection.

In addition, the new metallized or metallized/brazed layers have good wetting characteristics, with wetting angles of less than 5° or even at 0°. Further, the metallizing or metallized/brazed layer penetrates and seals all surface pinholes, microcracks, or other defects in the ceramic at the interfacial bonding region. These defects are thus converted from crack-initiating points, surfaces, or regions into strengtheners. A thick (over 20 to 100 microns thick) metal layer of controlled residual stress can compress the ceramic thereby further toughening the brittle ceramic. Graphite or carbon fibers or particles may thus not only be oxidation resistant but surface toughened and made non-brittle.

The invention also leads to a new generation of "high-fidelity" machining tools made of diamond, alumina, zirconia, boron carbide, BN, SiC, $Si_3N_4$, zirconium carbide, $TiB_2$ (melting point 2900° C., and TiC (melting point 3146° C.), zirconium carbide, or other hard ceramics. With the new method, these ceramics are microscopically defect-freely and tenaciously joined to rigid metals including inexpensive carbon, stainless, tool, or other alloy steels, or even tungsten or other carbides. In present clamped-on or screwed-on ceramic tool bits, the fragile ceramic is already severely prestressed even when the tool is not in use. Maximum useful stresses cannot, therefore, be applied during actual usage. Further, with each thermal fluctuation or mechanical vibration, the tool becomes looser and looser due to metal yielding and fatigue.

In contrast, the new tools of the present invention are, except for the favorable compressive residual mismatch stresses mentioned above, not prestressed locally and will not work loose under any conditions. Also, in contrast to other bonded ceramic tools, the bonding regions in these new tools are defect-free and actually strengthen the diamond or ceramic, because of sealing of surface defects on the ceramic and because of the residual compressive surface stresses from the more shrinking metallized metal layer relative to the ceramic, as shown above. These residual stresses are functionally graded, with its highest value precisely at the ceramic surface wherein maximum protection is required. The metallize/braze perfectly wets and bonds the ceramic even on the microscopic scale, fully microsupports the ceramic or diamond tool tip, and prevents the ceramic from moving, deforming, vibrating, or fracturing. Hence, even under extreme vibrations, heavy loads, or thermomechanical shocks, the machining forces, positions, and motion are transmitted directly and with high fidelity to the very tool tips. Greater machining accuracy, less tool chatter, wear and breakage, and longer tool life and reliability are possible.

Natural or synthetic diamond is rigid, noncontaminating, and chemically stable, readily cut to precise sizes, and easily cleaved and polished to microinch finishes. Excelling also in electrically insulating and thermally conductivities, it thus is a potential heat-sinking substrate for high-power laser, microwave, and fast-switching VLSI circuits. This leads to the densest packing, best high power, high frequency, high temperature, and radiation-hard devices. When developed, diamond circuits could operate at up to 600° C. or 475° C. higher than Si or GaAs, respectively.

The common method of metallization in semiconductor contacting, or for bonding diamond to copper for diamond heat sink application, consists of first sputtering a layer of 600 Angstroms (A) of active metal titanium, followed by 1,200 A of platinum and one micron of gold. The titanium bonds to the diamond, while the gold bonds to the metal. The platinum is a diffusion barrier to prevent interaction between titanium and gold. The preparation of a diamond heat sink for electronic circuits requires expensive equipment and six critical Ti—Pt—Au-bonding processing steps for bonding the top and bottom surfaces of the diamond. The entire bonding process is costly, complicated, and degrading to the product. Yet the product often fails because of peeling, blistering, intermetallic formation, and unwanted reaction between different phases.

As shown above, sputtered deposits usually contain pores, voids, surface contaminated grains, weakly bonded regions, and microcracks particularly on large-area deposits. The bonding between the substrate and deposit is therefore far from being metallurgically perfect. In addition, the abruptly graded and multiple serially bonded (C—Au—Pt—Ti) layers suffer seriously in two respects because:

1) The mechanically, chemically, and thermally (particularly for diamond heat sinks) weakest layer, no matter how thin, controls the entire bond—Law of the Chain, namely, the strength of a chain is determined by its weakest link; and 2) During any processing or service, the slightly possible existence of severe mismatch stresses between different layers, due to a pore, void, or microcrack, or a single weak, brittle, or unstable phase in the entire relevant phase diagrams at any temperature or time, no matter how transient, can totally destroy the entire joint—Murphy's Law, namely, any slightest possibility of failure of a system is often the very cause of the system failure.

According to Amer. Soc. of Metals' Binary Alloy Phase Diagram, T. B. Massalski, Editor, 1990, p.1182, Au and Ti form four intermetallic compounds: $Ti_3Au$, TiAu, $TiAu_2$, and $TiAu_4$. Similarly, C and Ti form TiC and $Ti_2C$; while Pt and Ti form $Ti_3Pt$, TiPt, $Ti_3Pt_5$, $TiPt_3$, and $TiPt_8$. These intermetallics have high thermal and electrical resistivities, are weak and brittle, change volume during their formations, and often differ in thermal expansion coefficients compared to diamond or C, particularly at high temperatures. The formation of these intermetallic compounds provide many opportunities for the above laws of the Chain and Murphy to operate adversely, drastically reducing the joint reliability. The intermetallic compounds formed in ternary systems such as C—Ti—Pt, C—Ti—Au, Ti—Pt—Au, Ti—Pt—Cu, . . . are even more complex, and mostly unknown.

Hence, the active metallization methods (with Ti, Zr, Nb) in general, and Ti—C method in particular, usually give unreliable products with weak strength and poor thermochemical stabilities. The many complex and costly Ti—Pt—Au-bonding processing steps present formidable technical challenges that have so far failed all materials scientists worldwide. Thermochemical instability may render the Ti—Pt—Au—Cu system unreliable. The National Materials Advisory Board concluded in 1990 that metallization "will be the predominant failure mechanism" in future diamond (and SiC) electronics. See attached copy of the relevant portion of the DTIC Report Ad-A222,986, p. 81. According to Laser Focus World, Vol. 29, p. 50, 1993, the Japanese engineers in the Ministry of International Trade and Industry (MITI) and the Japan Fine Ceramic Association have also stressed the need for more research in diamond bonding and film making for new diamond-based products. Since diamond film making involves bonding the diamond both to diamond itself and to the substrate, the difficulty of an improved bonding method for diamond is thus evident.

In contrast, the phase diagrams of diamond or carbon with Fe, Mo, W, and Si are relatively simple. Stronger carbon-metal joints with high temperature resistance and thermochemical stabilities are therefore possible. The laterally graded seals of the invention, i.e., graded metal-ceramic microjoints in parallel, do not have these two problems associated with the Chain and Murphy Laws. See U.S. Pat. No. 4,890,783.

A modified W/Mo-based metallizing process can be used to perfectly bond diamond to copper. $MoO_3$ powders are used, together with CuO to supply the braze metal. A low-melting metal such as Sn, Zn, Pb, In, Sb, and Bi can also be used to replace the Cu to further lower the melting point of the braze in the bonding layer and to prevent melting the substrate metal (Cu or Ag). As an example, with a $MoO_3$—CuO—$Bi_2O_3$ (volume percentages typically of 40–80:10–50:5–15 and preferably 60:30:10) of metallizing process at about 1,000° C. for 10 minutes, it is possible to produce, without any use of Ni, Co, Ct, Ti, Zr, Nb, Pt, or Au, to produce a microscopically perfect, tough, tenacious metallized layer on both the top and bottom diamond surfaces in a simple, reliable, low-cost single-step metallizing/brazing method. The bottom metallized surface can be bonded to the copper substrate for forming electrical and thermal contacts on selected bottom, top, and side surfaces of the diamond, all in the same single processing step.

The metallizing/brazing liquid produced in this diamond bonding method not only microscopically wets and seals crack-initiating surface defects, but replaces surface voids and microcracks with solid, thermally highly conducting copper. This bonding method also produces a single-phase, dead-soft annealed copper braze bonding region extending all the way from the diamond to the metal substrate. There are no microscopic or macroscopic pores, voids, cracks, and second-phase materials in the interfacial bonding regions.

The eutectic or carbide-forming method disclosed above is suitable for bonding carbon-based ceramics including diamond, with single element Fe, Si, W, and Mo, as previously described. Instead of heat-sinking copper as the substrate, other thermally conductive substrate materials are equally useful. These materials include Ag, Au, Pt, Ni, silicon nitride, silicon carbide, aluminum nitride, graphite, thermally conductive composites, and barilla.

The copper braze, produced at near the melting point of copper, is thermochemically highly stable, and electrically fully aged and burned in. It has unsurpassed temperature resistance (850° C.), has low electrical resistance (no more than 150% of that of pure copper), and absorbs the mismatch stresses for stabilized carrier mobilities in the semiconductor chips. The electrical characteristics of the electrical circuits mounted on these diamond heat sinks are thus highly stable and predictable.

The electrical resistivity of Cu, Ag, Au, Pt, and Ti at 20° C. are: 1.67, 1.59, 2.35, 10.6, and 42 microhm-cm, respectively. The thermal conductivity of Cu, Ag, Au, Pt, and Ti at the same temperature are: 0.941, 1.0, 0.71, 0.165, and 0.04 cal/sq cm/cm/°C./sec, respectively. The Young's modulus of Cu, Ag, Au, Pt, and Ti are: 16, 11, 11.6, 21.3, and 16.8 million psi/sq in, respectively. The single-phase braze metals, such as Cu, Ag, and Au, used in the diamond-metal bonds in the new diamond heat sinks, give high thermal and electrical conductance of the new diamond heat sinks. The thermal or electrical resistivity is no more than 200% that of the pure braze metal Cu, Ag, or Au. The Young's modulus of the dead-soft braze is also no more than 200% of the pure braze metal to provide the critical stress relief means for these diamond-metal bonds. The Young's modulus of the melted and refrozen, dead-soft braze metals such as Cu, Ag, and Au are low, no more than 140% that of the respective pure braze metal, compared favorably relative to the sputtered, surface-contaminated and high-velocity cold-worked and high-resistivity Ti, Pt, and Au particulate layers normally used in bonding diamond, SiC, and other ceramics.

The remarkable strength of the new diamond-metal bonds is clearly shown as follows: in preparing for microsections, cutting even a 1.5-mm diamond grain represents great difficulties. It generally requires three diamond cutting wheels rotating at 2,000 rpm for three days. Instead of the diamond wheels cutting the small brazed-on diamond grain, this single brazed-on diamond grain is actually cutting the millions of diamond powders bonded by other methods on the diamond cutting wheels, while sustaining 8.6 million severe mechanical shocks. The new bonded diamond grain thus forms excellent machining tools for cutting, milling, grinding, polishing, . . . .

By replacing the Cu and CuO by Ag and AgO, respectively, in the metallizing/brazing composition, and by reducing the metallizing temperature by about 120° C. for the lower-melting silver, diamond heat sinks have also been made with silver substrates. Silver is the best metallic conductor, both electrically and thermally. As shown before, the metallized surface may be gold plated for high-temperature oxidation resistance. Alternately, the Cu and CuO can be replaced by Au and gold chloride, respectively, with a suitable adjustment in the metallizing temperature. The metallized diamond can be braze-bonded to Pt, Pd, and other precious metals, if needed. W and $WO_3$ or mixed W/Mo and $WO_3/MoO_3$, respectively, may be similarly employed. The substrate material can also be Pt, Pd, Au, Ag, or even BaO, AlN, graphite, silicon carbide or nitride, or thermally conductive composites. Diamond can be brazed onto these thermally conductive substrates if it has a metallized bottom surface.

Unlike the conventional C—Ti—Pt—Au system, the diamond heat sinks of the present invention have thermodynamically stable material systems and can safely be used above 630° C. The C—Mo—Cu—Bi system has been in liquid thermal equilibrium for over 10 minutes at the brazing temperature of about 1,000° C. The bond is thoughly thermally stabilized, because the liquid processing at the high temperature metallizing/brazing gives the same diffusion length as that due to the solid diffusion at the operating temperature of 600 or 630° C. for tens of years.

These new diamond heat sinks dissipate heat both vertically by heat sinking and sidewise by heat spreading in the diamond. Heat can also conduct into a side metallized metal layer, or even into a neighboring similarly bonded diamond body on the other side of the side metallized layer. This neighboring conductive diamond body may be replaced by metal or other conductive ceramic such as BeO. Because of the excellent wetting, there is no air gap or pores between the diamond and the metallized layer and between the metallized layer and the conductive body. Nor are there any insulating microcracks to stop heat propagation vertically or horizontally. In particular, no insulative air layer exist between the diamond and neighboring diamond body.

The neighboring conductive body of diamond or metal may have a height at least 0.5 or 1 mm higher than that of the diamond. The side metallized layer intentionally extends substantially (over 0.5 or 1.0 mm) above the top surface of the metallized diamond body so that the outward heat spreading from the diamond has a significant component in a sidewise upward direction. There must absolutely be no air gaps, voids, or microcracks, because these defects destroy the critical vertical heat sinking or lateral heat spreading properties. Yet CVD thin diamond films have periodic vertical cracks due to the unavoidable dynamic mismatch stresses. See Narayan et al paper mentioned below.

The neighboring conductive body may be another diamond body. This second body may also be microscopically perfectly bonded metallurgically onto the same material substrate. The two diamond bodies then share the same, single metallized bonding layer, thereby minimizing thermal and electrical resistances. A new integrated diamond heat sink then results, and can even be achieved in the same single-step metallizing/brazing operation by applying one or two layers of the same metallizing/brazing composition on either one or both side surfaces of the adjoining diamond bodies. Upon heating to the high metallizing temperature, these two bodies can be joined together by a common single-phase braze material of pure or relatively pure braze metal. In all these operations, no external force is required to push the diamond bodies together during the metallizing/bonding process.

Preferably, the common side metallized bonding layer is no more than about three mils (0.076 mm) or one mil (0.0254 mm) thick to maximize the lateral heat spreading from one diamond body to the other. The top and side metallized bonding layers on the two diamond bodies may all terminate to have a common coplanar top surface to provide a "coplanar" diamond heat sink for the mounting thereon of a fragile semiconductor or superconductor chip or integrated circuit. In this design, the bottom area of the circuit chip is greater than the top area of either diamond body but smaller than the combined top areas of both diamond bodies. Hence, one part of the electronic chip or circuit is mounted on one of the diamond bodies, while another part of the same chip or circuit is mounted on another one of the diamond bodies.

As shown, with the solution metallizing method disclosed elsewhere in this specification, the thickness of the bonding layer may be easily controlled simply by diluting the solution concentration. Extremely thin bonding layers, from 10,000, 1,000, 100, down to 10 Angstroms, are then possible, with the thickness controlled to within 100 or 10 Angstroms. The common planar top surface of the coplanar diamond heat sink can also be thus made to have a height accuracy of 1 micron to 100 or 10 Angstroms to facilitate the mounting the electronic chip or circuit.

A larger number of diamond bodies can be similarly joined together, all sharing a common planar top surface. A large or very large, integrated planar diamond heat sink, for mounting thereon a much larger, high-power, high-density, high-frequency chip than a single diamond body can accommodate. This procedure solves the critical problem of diamond size and cost. The diamond cost increases exponentially, not proportionally, with its size. The new diamond heat sink is significant in that useful diamond heat sinks of any reasonable sizes are available right now, while practical diamond films may still be years away, as shown immediately below.

Many trials have been made to make electronic diamond circuits or heat sinks by thin film methods. The most advanced method is to use a laser synthesis method to produce single-crystal, epitaxial diamond films on copper substrates. See, Narayan et al's article in the Apr. 19, 1991 Science magazine, pp. 416–418 (Exhibit D). Scientists have hailed this technique as a revolutionary breakthrough. See Editorial in the April 1991 issue of Science magazine.

Figure 2A:
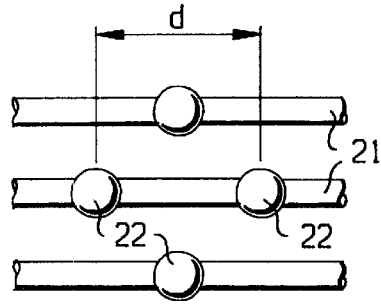
FIGS. 2a–2b show nodular bonding spots on reinforcing carbon fibers in carbon composites.
Figure 2B:
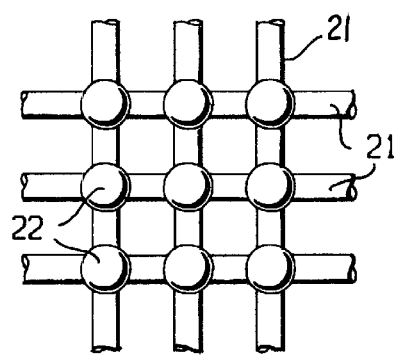

However, since these epitaxial films are thin (500 A), and have perfect areas of only two or three microns in sizes. The films are still imperfect (with severe transient stresses causing periodic parallel microcracks 9 microns apart, as shown in FIG. 2b of the article. Useful diamond heat sinks may be difficult to achieve for practical circuits, which are over tens of microns in size. In diamond heat sinks, lateral heat spreading is over twice as important as vertical heat sinking. The periodic parallel microcracks, however, form vertical insulating walls, destroying heat spreading. The result is that no diamond film is actually better than any diamond film, since this film always has its own resistance in addition to the associated high resistances of the various Ti, Pt, Au bonding layers.

In his paper on "Diamond Metalllization" published in Proc. Diamond Materials, Proc. 93-17, Electrochemical Society, Eds. J. Dismukes & KV Ravi, pp. 605–612 (Ref. E), Li shows that diamond is the most difficult ceramic material to bond, for the following reasons:

1) Diamond has zero thermal expansion coefficient, giving the maximum thermal expansion mismatch when bonded to any material;

2) Diamond has maximum rigidity or Young's modulus, resulting in maximum mismatch stresses, which are the product of mismatch strain and Young's modulus;

3) Diamond has the highest thermal conductivity, generating the maximum temperature differential and critical dynamic mismatch stresses as shown in the U.S. Pat. No. 4,890,783; and 4) Diamond is the most chemically inert or non-contaminating material, producing the minimum thickness of interfacial bonding region and maximum mismatch stress and strain gradients.

Further, these difficulties multiply each other rather than merely add together. The bonding of any ceramics is already very difficult as shown in, e.g., Ref. A, and repeated failures of many U.S., Germany, and French major programs. Yet, if each of these four factors further doubles the bonding difficulty, the combination thereof does not increase the bonding difficulty merely addictively, or 2×4=8 times; but multiplicatively, or 2×2×2×2=16 time.

These difficulties are confirmed by Refs. A–E. Also, as shown above, the most common diamond bonding method is still the costly, complex, and difficult active method using sputtered Ti—Pt—Au layers, borrowed from the semiconductor industry. On these multiple, active thin metal layers, the Laws of Chain and Murphy operate to give unreliable, low-quality, and thermally unstable joints, as observed. Hence, despite the many patents and articles on the topic, diamond bonding has been a universally recognized, very difficult problem worldwide. Any significant progress in the field, particularly for the critical diamond electronics and heat sink applications, would therefore appear to be more patentable than in even other chemical cases.

As shown above, it is very difficult if at all possible, to employ the conventional methods to make microscopically bonded, uncontaminated but functionally graded, void-free and crack-free thin diamond films of any reasonable sizes (e.g., 1.5 mm). Modification of the filming technique, whether physical or chemical, with high or low voltage, pressure, temperature, concentrations in the gas compositions, . . . , or even different substrates, simply would not minimize or eliminate the many diamond bonding problems mentioned above. This has, of course, been verified, empirically and independently, by the U.S. National Material Advisory Board and the Japanese engineers and scientists, as shown above.

The laterally graded seals, or graded metal-ceramic microjoints in parallel, as described in U.S. Pat. No. 4,890,783, provides a new solder preform for mounting semiconductor or superconductor chips on the diamond heat sinks. Note that the central region of the preforms has the purer, softer, and more conductive metal than the peripheral regions. This new preform thus usefully manages the thermal dissipation, dynamic mismatch stress, and electronic circuit stability, all critical to modern electronics. The new diamond heat sink and this new preform form, in combination, a two-stage heat-sinking system.

Diamond has the highest thermal conductivity, breakdown voltage, saturated velocity, and radiation resistance but lowest permitivity. Combined, these parameters yield the Johnson figure of merit for the power and frequency performance, and the Keyes figure of merit for the speed, of a transistor manufactured from diamond. These figures of merit are respectively 8,206 and 32.3 times higher for diamond than they are for silicon. High-density, diamond active circuits, if perfected, can operate at up to 600° C. or 475° C. higher than Si or GaAs, respectively, eliminating cooling equipment now occupying, e.g., much volume of the average satellite.

However, serious material and processing problems still exist, partly as shown above. Presently, only p-type conductivity can be obtained at useful current level by implanting boron. The evidence of n-type conductivity is not convincing. Even at 1,450° C., it is difficult to completely anneal the heavily damaged regions of the implanted diamond. Most of the n-type conductivity was lost after prolonged annealing. The results of ion implantation are further complicated by the fact that the radiation damage introduces donors and acceptors in equal concentrations. To date, only n-type diamond samples were made by ion implantation of lithium into natural diamond.

A new diffusion procedure is disclosed here. Essential to controllable, uniform diffusion doping is the high effective processing temperature, intimate microscopic contact of the doping source to diamond, and formation of possible diamond-metal doped eutectics which are molten at the processing temperature (See graphite-metal bonding in this specification). A perfect wetting of the diamond with a liquid diffusion source then obtains. In contrast, the conventional doping methods use low-temperature, imperfect contacting, and solid diffusion sources.

The unreliable diamond wetting and bonding, and extremely slow and uncontrollable problems of diamond diffusion can be solved by using a modified W/Mo-based fusion metallizing method. This diamond doping method employs a metallizing/brazing/contacting composition with 40–60 v/o (volume percent) Mo, 10–30 v/o Cu and 5–15 v/o Bi for processing at 900–1170° C. The composition is also an effective diamond doping source. This combined diamond bonding and diffusion method is even useful for other high-temperature semiconducting ceramics such as silicon carbide or nitride.

This new method also solves the problems of low solubility of potential atomic dopants in diamond. The method is extremely simple, and provides ideal conditions for controlled contacting and diffusion for diamond by achieving many purposes:

1) Atomically cleans the diamond surface;

2) Perfectly wets the diamond even on the microscopic scale;

3) Defect-freely bonds the diamond upon cooling;

4) Seals porosities, microcracks, and other defects in the diamond surface region, and thereby increases the thermal and electrical conductivity, contact surfaces (for, e.g., improved effective mass and thermal diffusion areas and rates) and toughens and strengthens the diamond;

5) Due to the high processing temperature, provides dead-soft shock-absorbing metal layer on the surface, thereby maximizing thermochemical stability, minimizing thermomechanical stresses on, and stabilizing carrier mobilities in, the semiconducting diamond (or SiC);

6) Supplies low-resistance electrical and thermal contacts to the diamond; and

7) Preages and burns-in the metallization contacts. Diamond metallization, according to the DTIC report mentioned above, will be the predominant failure mechanism of high-temperature semiconductors (SiC, diamond).

The same fusion metallize/braze composition can also serve as n-type dopant source for diamond, by simply adding n-type dopants in the W/Mo-based metallizing/brazing medium. As usual, elements in the Fifth Group of the Periodic Table such as N, P, As, Sb, Bi, V, Cb, Ta, Pa; elements in the Sixth Group (O, S, Se, Te, Po, Cr, Mo, W, U; and possibly elements in the Seventh Group (F, Cl, Br, I, At, Mn, Tc. Not only metals such as As, Sb, Bi, W, Mo, . . . , but oxide, nitrides, phosphides, sulfides, phosphates, fluorides, arsenide, arsenates, . . . are useful as n-type dopants in the modified W/Mo-based, combined metallizing/brazing/contacting/doping process. This W/Mo-based process already contains such N-type dopants as W, Mo, and oxides.

To make the doping more effective, multi-doping techniques are preferred, e.g., oxides of copper, antimony, phosphorous, arsenic fluoride, bismuth phosphates, . . . as both the braze and multiple dopants. There are other possibilities. Oxygen and nitrogen, for example, form compounds, eutectics, or other phases with many metals, also for use as the potential dopants. The potential doping possibilities further explode. In addition, the Cu—O phase stability diagram shows that at a given temperature, the partial pressure of oxygen and solubility of oxygen in copper is very low even at the metallizing temperatures of up to 1,050° C. But $Cu_2O$ has much higher partial pressures and apparent source solubility. CuO has even higher solubility, in fact, five orders of magnitude higher at the metallizing temperature. Copper is a key ingredient in the new metallize/braze composition. If it is a strong P-type dopant, one can replace it with, e.g., Sb, or As.

Control of the wettability, dopant source concentration, and the properties of diffusion region and metallized interfacial region, as to, e.g., their thicknesses, effectiveness, and properties, may be achieved by regulating the metallizing compositions, solution concentrations, temperatures, and times. Lower metallizing temperatures and solution concentrations, higher melting points of the compositions, or shorter processing times give less doping effects and thinner and less diffused interfacial region, and vice versa.

Because of the high-temperature liquid diffusion, the diamond metallizing processing steps fully stabilizes, preages, and burns-in the diamond and, therefore, generates very reliable metallization contacts. There will also be no dopant outdiffusion and redistribution, because of the thermodynamic equilibrium of constituents even at the high metallizing/doping temperatures. This is in sharp contrast to ion implantation in which the dopant atoms are barbarously forced into the semiconductor with high voltage and momentum, with high divorce rates and unstable results thereafter.

Most conventional doping processes for diamond employ only solid-state diffusion, with diffusion coefficients $D_s$=1.E-10 to 1.E-20 cm$^2$/sec, 5–16 orders of magnitude smaller than liquid diffusion. For the same processing time, the solid diffusion length of down to 0.32 A is several orders of magnitude shorter than the new liquid diffusion case and insufficient for device making.

Because diamond has very high melting point, the ratio of the absolute diffusion temperature to absolute melting point of diamond is very low in conventional diamond diffusion, which has low effective diffusion temperatures. Even the solid diffusion coefficient must therefore be near the lower end of the diffusion rates, possibly even nil. The diffusion length is therefore sub-Angstrom and generally unmeasurable.

The new metallizing/brazing/diffusion process of this invention employed for 10 or 20 minutes would require tens or hundreds of years of solid diffusion at the usually used "low" diffusion temperatures to achieve the same diffusion results. Comparatively, then, a practical, very fast diffusion source is now possible with the new diamond doping method.

This new method greatly simplifies the diamond bonding/diffusion method because it: 1) achieves high-temperature thermodynamic equilibrium of component materials, 2) transforms diamond defects into reinforcements, and 3) minimizes static and dynamic mismatch stresses, yielding a vastly superior product. This simplified processing technique combines the metallizing, brazing, contacting, diffusion, and high-temperature pre-aging, burning-in, and diamond diffusion steps into one operation. The pre-aged or burned-in connections are important in overcoming the predominant failure mechanism in diamond electronics due to improper metallization referred to above. For the critical diamond active semiconductor or heat sink applications, the microscopically perfect wetting and bonding of diamond by metal maximizes contact area, thermal conductivity, and conductance. The single-phase low-modulus or dead-soft annealed braze absorbs mismatch stresses and strains, assuring high thermochemical stability, thermomechanical shock resistance, and uniform, stable carrier mobilities and predictable circuit characteristics.

Still other applications of the specially bonded diamond are possible. High performance missile domes and optical components require ultrahard materials such as sapphire, spinel, or diamond. Such materials are presently fabricated using diamond abrasive grinding and polishing. This process is slow and very expensive, and results in subsurface damage of the substrate. This damage directly limits optical and rain erosion performance.

In the conventional diamond grinding and polishing wheels, the diamond abrasives are not perfectly or defect-freely bonded, as shown above. The defective bonding, as well as surface defects in the diamond itself, allows the diamond grains to move, deform, vibrate, and fracture erratically; and creates random, unwanted modulations of the signals on the programmed finishing forces, torques, positions, and motions. Hence, the finishing process is out of control. Precision diamond finishing is costly, nonreproducible, and even impossible. Lengthened polishing time, rapid tool wear and vibrations, abrasive grain tear-off, and poor surface finish result.

It is therefore desirable to make special "high-fidelity" diamond grinding and polishing wheels according to the new diamond bonding technology. The meaning of "high-fidelity" has already been described above. This unique technology has already produced tenacious, defect-free and thermomechanically shock-resistant bonding layers. These layers microscopically perfectly wet, bond, and microsupport the diamond abrasives, as shown above, eliminating the unwanted modulations of the signals on the programmed finishing forces, torques, positions, and motions.

The new diamond metallizing process also produces the required diamond abrasive coatings on the new grinding and polishing wheels. The process provides perfectly and rigidly braze bonded diamond abrasives layers onto a hard substrate such as carbon or tool steel, or even tungsten or silicon carbide. The metallizing liquid seals all crack-initiating surface defects on the diamond film, provides full, rigid metal microsupport for every diamond grain during the polishing operation. This feature minimizes induced microscopic bending moments and tensile or shear stresses due to the polishing forces. Hence, even under extreme vibrations, heavy loads, high feeding rates, or mechanical shocks, the finishing forces and motions are transmitted directly and with high fidelity to the tips of all the macroscopic or microscopic abrasive grain tips. Greater finishing accuracy, less diamond wear, chatter, and breakage, and longer wheel life and reliability is therefore possible.

This same method can be used to prepare other high-fidelity machining tools such as those for milling, machining, drilling, and the like, or for ultrahard materials other than diamond such as boron nitride, boron carbide, alumina, silicon carbide, . . . These ultrahard materials can also be surface finished by grinding and polishing wheels made by bonding of a hard metal (e.g., W) or hard ceramic material including diamond.

Most natural diamond and deposited diamond films still contain many defects such as (111) twins, impurities (nitrogen, nickel, iron, aluminum, and carbon isotopes), porosities, dislocation, stacking faults, grain boundaries, segregated constituents, inclusions, and unwanted phases (such as carbon). All these defects make the diamond film weak, brittle, and sensitive to mechanical vibrations and shocks. Any microcrack, discontinuity, or impurity particle in the diamond film may initiate localized catastrophic failures. These localized failures degrade the product quality, shorten the finishing speed, and cut short the finishing tool life. Hence, all these defects must be sealed, eliminated, or neutralized. This the newly invented coating method will do.

Specifically, the metallizing/brazing liquid of this invention seals microscopic crack-initiating surface porosities and other defects, and produces a single, microscopically perfect braze-bonded structure. These conditions ensure rigid support to all the diamond abrasives during service, but minimize mismatch stresses and stress gradients and maximum toughness, adherence, and thermomechanical shock resistance during use. As discussed above, the resultant liquid-diffusion formed metal-ceramic bonds are totally different from those formed by mere compacting, evaporation, sputtering, plasma spraying, sintering, infiltration, chemical vapor deposition (CVD), physical vapor deposition (PVD), . . . CVD diamond films, e.g., may contain up to 20% porosities, according to the U.S. DTIC report referred elsewhere in this application. Any porosity degrade the diamond (or other ceramic) heat sinks as to thermal conductivity, strength, toughness, and reliability.

Another application of the new diamond bonding process relates to poly-crystalline diamond films. These films are grown by plasma enhanced chemical vapor deposition, which offers a means to protect infra-red window and dome materials in severe environments. The deposited diamond have large grain sizes and random crystal orientations which contribute to reduced optical performance because of scatter. Polishing of the growth surfaces is necessary to reduce the scatter effect. However, the large grains and random orientations make it difficult to polish these films to high qualities at low cost, particularly for large curved surfaces up to two inches in diameter. The new metallizing/brazing method gives microscopically perfectly bonded metallized layers for the diamond and provides a tenacious, defect-free, rigid metal (alloys of Cu, Ni, Fe, . . . or even tungsten carbide in cobalt) layer totally embedding all the diamond grains. The metal layer cements together the diamond grains, seals all surface defects, toughens and strengthens the diamond film or layer, firmly microsupports every tiny diamond grain during polishing, and minimizes induced bending moments and tensile or shear stresses on the fragile diamond grains during polishing.

Diamond is transparent to laser. Hence, the metallizing/brazing of diamond to metal can be performed with pulses of high-intensity $CO_2$ or other laser. The laser beams transmit directly through the diamond without causing much heating, but heat up the metal (steel, Ni, Si, GaAs, . . . ) to form joints of precise sizes at exact locations with precise laser pulsing and heat input within seconds or milliseconds. The bonding can be done in any ambient including vacuum, neutral, reducing, or even oxidizing, at below the melting point of a low-melting substrate because of the repeated and controlled, very localized millisecond or microsecond laser pulses.

With the method of this invention, sapphire, quartz, alumina, or zirconia tubes can be sealed vacuum-tightly to niobium, tantalum, or other ceramic tubes to make useful electronic cavity or optical windows for services to or over 1300° C., 1500° C., or still higher temperatures. The new bonding method will avoid the usual frits seals which are weak, contaminating, short-lived, deteriorating to electrooptical characteristics of the component, and otherwise unreliable in operations.

Defect-free or flawless coatings or bondings are also necessary to contain dangerous materials, and should be used to replace weldments which almost always have bubbles, oxides, inclusions, segregation patterns, severe residual stresses, weak grain boundaries, or other defects.

The strong, defect-free, and thermomechanically shock-resistant quality of the metallized layers on ceramics, graphite, diamond, and reactive metals such as titanium, zirconium, aluminum, or stainless steel is especially important in the manufacture of advanced composites. Here, the reinforcement may be fibers, particulates, sheets, or two- or three-dimensional weaves of the ceramics, graphite, boron, oxides of aluminum or zirconium; and carbides or nitrides of Ti, Zr, Hf, V, Nb, Ta, Cr, Mo, or W; borides of carbon or nitrogen; silicides, aluminides, other intermetallics; diamond; and metals. The reinforcement is then perfectly wetted by and bonded to the matrix of metals, ceramics, carbon, borides, nitrides, carbides, diamond, . . . matrices. Good interfacial bond strengths in, e.g., about 20 to 60 volume % graphite, SiC, or $Si_3N_4$ fibers or particles in Type 6061 aluminum, alumina, or zirconia reinforcement, allow load transfer to occur between matrix and reinforcement thereby giving maximum specific moduli and strengths. These defect-free bonding at the interfaces prevents debondings and allows ideal load transfer between, within, and along the reinforcement members thereby achieving maximum strength, production yield, and productivity at minimum costs.

Coated with the new metallized/brazed films up to 1–2 or 5–20 microns thick, ceramics, boron, graphite, diamond, or glass powders or fibers 0.5 through 50 to 200 microns in diameters, are also suited for specific particulate reinforced composites. Upon compacting and sintering these metal coated particles to proper densities and mechanical properties, special acoustic or otherwise damping materials are obtained. Because of their excellent wetting properties, these specially coated fibers or powders produce better liquid infiltrated composites with physical, thermal, and electrical properties superior to those of any existing composites.

Even mismatch ceramic-metal joints made according to the present invention refused to fail under repeated, rapid and severe thermomechanical shocks. Further, the final forced fractures occur away from the bonding regions. This shows that the bonds are free of flaws, microcracks, inclusions, and other defects, as confirmed by microphtos.

In many composites, weight is a critical consideration. Because of the heavy densities of W and Mo, a very thin W/Mo-based metallized/brazed layer, down to several atomic layers in thickness, may be used with or without any copper, nickel, or other braze metal. The formation of a surface liquid diffusion layer 3 to 30 atomic layers (about 10 to 100 A) takes only $10^{-9}$ to $10^{-7}$ seconds, if a liquid diffusion coefficient of $10^{-5}$ cm×cm/sec is used. The control of such extremely thin layer can be achieved by applying a thin layer of a weak or very weak metallizing solution containing limited but exactly controlled amount of molybdate or tungstate compounds.

For example, sodium molybdate ($NaMoO4.2H_2O$) has a molecular weight of 241.95. Each mole of this compound contains 1 mole or 95.95 grams of Mo. Applying a 0.1 molar solution (0.1 mole per 1,000 cc) of this compound to form a 0.1 mm thick coated layer gives a Mo concentration of 0.096 mg per square centimeter, with a final Mo layer thickness of $9.4 \times 10^{-6}$ cm or 940 Angstroms, in the coated or metallized area. If the sodium molybdate metallizing solution is diluted to a strength of 0.01, or 0.001 moles per liter (1,000 cc), the Mo concentration is then only 94 or 9.4 Angstroms, respectively. Thus, with the solution metallizing method, not only can the thickness of the metallized Mo layer be made to be less than 1,000, 100, or 10 Angstroms, but the metallized Mo thickness can also be controlled to a 1,000, 100 or 10 Angstrom accuracy. All this can be done by simply diluting the metallizing solution. Similarly, keeping the coated layer thickness constant at 0.1 mm but replacing Mo and $NaMoO_4$ by, e.g., Fe and $FeCl_2$, respectively, the 0.1, 0.01, and 0.001 molar metallizing solutions will provide Fe layer thicknesses of 710, 71, and 7.1 A, respectively, since Fe has atomic weight of 55.85 g and a density of 7.87.

Another problem with composites is that ceramic, graphite, and carbon fibers are very difficult to be perfectly wetted by, or bonded to, metals, other ceramics, or even to epoxy. Because of this difficulty, an airplane or other vehicle made of these composites often structurally fails under cyclic environmental heat-moisture conditions. Under capillary attraction forces, rain or condensed moisture on the composite surface deeply penetrates, or is drawn in, along the tiny passageways in the unbonded or poorly bonded interfacial regions between the graphite or other ceramic fibers and the epoxy, metal, or ceramic matrix. The penetration is facilitated by air release in, for example, an improperly oriented one-dimensional reinforcement where water enters from the outside skin and move freely along the entire length of the fibers. The entrapped air is forced out of the inner surfaces. This fills the composite structure with water.

When the environment turns cold, the filled water expands on freezing, possibly into miniature ice wedges, disruptively enlarging the passageways and further debonding the reinforcement from the matrices. Repeated filling-expanding cycles destroy the composites. If a high-altitude airplane lands in a hot humid weather, moisture automatically condenses onto the very cold composite skin and similarly fills the passageways. The vehicle may take off again into the same freezing attitude where the filled water expands on freezing with disruptive forces. Multiple cycles of landing and high-altitude flying thus also destroy the composite.

By uniformly covering these fibers with flawless metallized W/Mo-based coatings, with or without brazing materials, the bonding between these coatings and the matrix will also be flawless. Deep penetration is then impossible. Periodic coating of all the strands of these fibers 21 along their lengths with nodular metallized spots 22 at a specific distance d apart breaks up the passageways into small compartments of length d (FIG. 2a). Water can now penetrate to no more than the same distance d below the composite surface. Dipping a two-dimensional or three-dimensional fiber weave into a W/Mo-based metallizing solution or paste, again with or without braze, preferentially coats only the intersections of the fibers with the metallizing compound to thereby form the required nodules for stopping deep water penetration (FIG. 2b). The size of the nodular metallized spots can be controlled by adjusting the viscosity and/or solid content of the solution or paste. Wetting control with the addition of acetone, alcohol, house detergent (e.g., Wisk) also helps.

The reinforcing graphite or other ceramic fibers selectively but perfectly bonded at the nodulated or coated spots in the composites achieve excellent load transfer between fibers, or even along the fibers in metal-matrix composites, but allow systematically and controllably unbonded or weakly bonded regions between the nodules to act as mismatch stress and strain relievers. This condition leads to excellent toughness and thermomecanical shock resistances.

The ceramic metallizing processes described in this invention also allow the brazing or coating of the internal or external surfaces of ceramics of controlled densities or porosities. More specifically, porous alumina, zirconia, silicon carbide, yttria, mullite, and cordierite have already been metallized with the new methods on either the internal pores, external surfaces, or both. Substantially 100% of the internal surfaces of the porous ceramic can be metallized. Ceramic filters for molten steel, aluminum, or other metals or materials are already in wide uses. But the difficulty of perfectly bonding these porous and weak filter ceramic medium to each other or to metals used for handling these filters make their uses costly, difficult, unreliable, and often dangerous. Bonding these ceramic filters to steel wires or plates with these new methods minimizes these handling problems.

Multi-stage ceramic filters of alumina, zirconia, silicon carbide, yttria, mullite, cordierite, glass, or other ceramics strongly bonded to the same or different ceramic with the same or increasingly finer pore sizes can now be joined together, one on top of the other. Metal-reinforced multi-stage filters can also be made for, e.g., added strength through metal strengthening; multiple-purpose separations of gases, liquids, or solids from one another through physical means according to size differences; absorption by carbon; catalytic reactions by platinum; liberation or desorption of gases such as oxygen, nitrogen, carbon oxides, or hydrogen from the bonded oxides, nitrides, carbides; materials for doping or addition to the molten metals or other materials; chemical separation of substances present in the same gas, liquid, or solid phases; and other special features functions.

Ceramic filters for air, gas, oil, transmission fluids, and cooling water on automobiles, diesels, power generating equipment, and other machineries are already available. Similar fluid-tight filters for various other fluids including molten metals such as steel or aluminum, or catalytic reactors can, with the new bonding method, be strongly attached to internal or external carbon steel or stainless steel containers, other metallic, carbon, or ceramic hooks, knobs, holders, fasteners, protrusions, strengtheners, friction contacts, or springy devices for easy handling or for forming fluid-tight enclosures without fluid by-passing or leakage at the peripheries.

Catalytic materials such as platinum alloys may be coated on the metallized layer via diffusion coating, brazing, electrolytic or electroless plating. Reactive materials such as yttria or CaO, can also be made porous by sol gel, or by controlled powder packing and sintering, to achieve any desired powder sizes and packing or sintered densities. Such reactive ceramic filters, properly bonded to metal structures, may be used, for example, to chemically remove weakening sulfur in high-quality tool steel poured through these filters.

An electric heater may surround, or be embedded in, the porous ceramic filter for periodical activation with electric ohmic heating to burn to ashes or gasify the materials remaining on the ceramic filtering medium. This achieves reusable or self-cleaning results.

Many other uses in differing industries of the new bonding methods are readily seen. These include ceramic composites, graphite composites, intermetallic composites, metal-matrix composites, coatings on ceramics, graphite, or metals, high-strength chemically bonded ceramics, and self-lubricating materials containing, e.g., lubricating talc, $MoS_2$, or graphite particles in iron, steel, copper, or nickel. The composites may involve reinforcing fibers or particulates of ceramics, intermetallics, graphite, or metals in a matrix of ceramic, intermetallic, graphite, or metal.

Using the metallizing methods described above, metallized refractory metallic compounds can be formed for uses as the matrix or reinforcement for composites. These compounds include: oxides of Al, Ba, Be, Ca, Cr, Eu, Gd, La, Mg, Ni, Pu, Ru, Sm, Sc, Si, Th, Ti, U, V, Y, and Zr; carbides of Al, B, Ba, Be, Ca, Hf, Mo, Nb, Si, Ta, Th, Ti, U, V, W, and Zr; borides of Ba, Ca, Ce, Hf, Mo, Ni, Sr, Ta, Th, Ti, U, V, and Zr; Sulfides of Ca, Gd, Sr, U, and Y; nitrides of Al, Hf, La, Nb, Nd, Sc, Si, Pr, Pu, Ta, Th, Ti, U, V, Y, and Zr; and aluminides of Fe, Ni, Pt, Be, and Ti. Particularly attractive among these compounds are: $Si_3N_4$, SiAlON, SiC, $Al_2O_3$, mullite, AlN, $B_4C$, $TiB_2$, and BN.

Light, strong, tough, and reliable structural Al, Mg, Be, Ti alloys in composite forms can thus be made with metallized graphite, SiC, or other ceramic reinforcement that will operate over 480° C.

Powders of a ceramic, carbon, intermetallics, or reactive metal may be similarly metallized to achieve flawless and microscopically perfectly wetting surfaces so that the sintered powder compacts or liquid metal infiltrated composites will have unusually high strengths, densities, and thermal conductivities. Such metallized powders can also be cast as particulate reinforcements or strengtheners. These same powders can be cast (by, e.g., hot squeeze method) to achieve net shape or near net shape into complex structures or components.

Figure 3A:
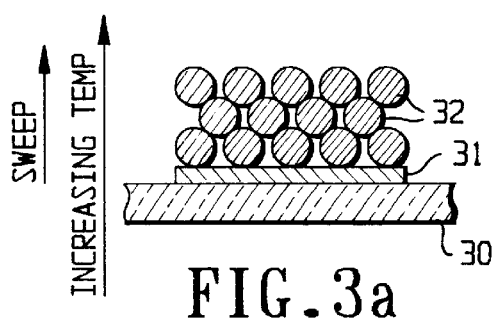
FIGS. 3a–3b show a multi-purpose bonding method for high temperature ceramic superconductors.
Figure 3B:
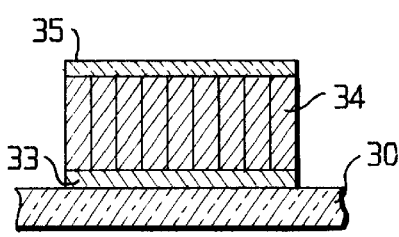

A multi-purpose procedure for bonding, sintering, purifying, densifying, strengthening, and otherwise improving the high temperature 123 ceramic superconductor, or other ceramics, is shown in FIG. 3. High temperature ceramic superconductors are superconductors which superconduct at above 90 degrees K. (Kelvin). In this multi-purpose procedure, a layer of a suitable $MoO_3$-based mixture 31 is formed at selected spots on a copper substrate 30, as shown in FIG. 3a. $MoO_3$ is the key ingredient in many of the new Mo-based metallizing operations. It melts at 801° C., but the melting point can be lowered or raised to selectable temperatures by forming alloys, eutectics, or compounds with, e.g., CuO, BaO, and $Y_2O_3$, and other oxides such as AgO, CaO, or TlO (Thallium oxide), or even fluorides, chlorides, or iodides in view of Ovshinsky's promising results on superconducting and particularly current-carrying capabilities in certain ceramic superconductors. Upon this $MoO_3$-based layer is spread the superconducting $YBa_2Cu_3O_{7-x}$ powders 32. A vertical temperature gradient is applied to the composite so that the top of the superconductor powders 32 is at least 20 to 50 C. below its melting point, while the bottom of the $MoO_3$-based layer is above the melting point of this mixture. This powders mixture layer will then melt, form the liquid-diffused bonding interfacial region 33, and sweep upward (FIG. 3a) to achieve the following highly desirable results:

1. Metallizing and bonding of the bottom layer of 123 superconductor to the copper substrate;
2. Temperature gradient zone-melting to purify the superconductor boundaries according to Pfann (See: Zone Melting, Wiley, 1966);
3. Vertically oriented, upward superconductor columnar grain growth 34;
4. Grain boundary scavenging, oxygenation, or halogen doping;
5. Liquid phase sintering of the superconductor particles for improved sintering speed, density, mechanical strength, and material stabilities partly also due to the purified or doped grain boundaries;
6. High critical current density of the purified, thinner, and oriented grain boundaries;
7. Cushioning or shock-absorbing qualities of the liquid-diffused, chemically and mechanically, functionally graded interfacial layer 33 between the superconductor film and substrate; and
8. Simple, low-cost, single-step and mass-producing but potentially high-yielding film-making operation.

After this special temperature-gradient multi-purpose operation, most of the impurities will be dissolved in the upwardly sweeping zone. This zone eventually comes up to the surface to be frozen into a highly impure layer 35. This impure layer can be removed by, e.g., grinding or chemical etching with mineral acids. See FIG. 3b.

Other high-temperature ceramic superconductors such as $Tl_2Ba_2Ca_2Cu_3O_{10}$ and $TlCa_2Ba_3Cu_4O_x$ can be similarly bonded or treated for properties improvement with the above method. The substrate does not have to be pure copper, but can be other metals such as aluminum, nickel, or iron, glasses, graphite, or diamond. Other ceramics such as $Al_2O_3$, $ZrO_2$, SiC, carbon, glasses, diamond, or even metals powders or filaments, may be similarly bonded onto metallic, ceramic, glass, or carbon substrates.

The ceramic layer 34 with thinned, purified, oriented grain boundaries have improved physicochemical properties including thermal and electrical conductivities. This is so because grain boundaries generally contribute to high resistivity. Low current density in high $T_c$ ceramic superconductors is still a major problem, particularly in polycrystalline, bulk or thick film materials. Improper grain boundaries are mostly responsible. This special multi-purpose bonding method also overcomes this problem.

In ceramic-metal joints other than for superconductor application, however, the above zone-melting procedure is harmful from the bond strength viewpoint. This is because the last-solidifying layer, usually of complex ceramic eutectic compounds, is weak and brittle and reduces the joint strength. The proper cooling direction after the metallizing here should, therefore, not be vertical but horizontal and laterally outward, as shown in FIG. 6. In this way, the last-forming layer is laterally swept out of the joint region into peripheral areas without harmfully affecting the joint strength.

According to the above disclosures, it is possible to microengineer the ceramic-metal, ceramic-metallizing layer, and/or metallizing-braze layers as to their thickness, and to have graded composition, thermoconductivity, and mechanical properties. The W/Mo-based metallized layer may be, for example, 10 to 20 or 30 microns containing a graded interfacial layer up to 5 or 10 microns. The effective liquid diffusion length described above may range from 5 to the entire 30 microns. These layers are obtained by liquid diffusion, generally through melting for over five minutes but up to one hour. The Cu, Ni, or other alloy braze layers may also be chemically, mechanical, and physically graded functionally, as described above.

Figure 4A:
FIGS. 4a–4d show newly microengineered microstructures of the bonding interfacial regions.
Figure 4B:
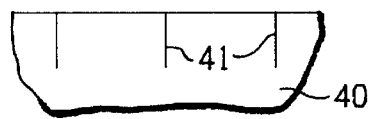
Figure 4C:
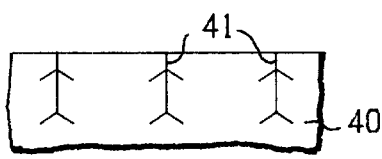
Figure 4D:
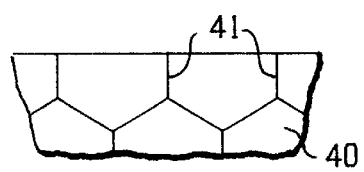

Another important grading of the interfacial layer relates to the microstructure. Many conventional joints rely on superficial adhesion, weak and defective chemical bonding, or mechanical anchoring with roughened surfaces. Rough surfaces increase surface area by about 41.4% with 45-degree slopes or valleys (FIG. 4a). An important feature of the new invention is the principle of rooting (FIG. 4b), branching (FIG. 4c), and networking (FIG. 4d). Straight roots of hard or soft metallizing materials 41 penetrate, during the metallizing or rapid liquid diffusion period, deep along the ceramic grain boundaries 40 in the ceramic. These roots may be in the form of fibers located at the intersections of the multiple boundaries, or in the form of sheets each located between two adjacent ceramic grains. These fibers and sheets may be straight, extending generally perpendicularly to the ceramic-metal interface (FIG. 4b). They may form branches following the grain boundaries (FIG. 4c). These roots may even flow deeply into the grain boundaries and turn or curve around to form a partial or complete network (FIG. 4d). The formation of these fibers or sheets depend on the surface energies of the metallizing compounds relative to those of the ceramic grains at the metallizing temperature. The depth of penetration also depends on these energies, but primarily on the metallizing temperature and time.

These penetrating metallizing materials, if harder than the ceramic, form reinforcement in a matrix of the ceramic material at the interfacial region. This can be achieved by selecting a W/Mo-based metallizing composition which, with the ceramic at the metallizing temperature, forms hard (with Mohr hardness of over 8 or 9 when solid, versus the usual less than 7 or 6 for the ceramic) tough, and strong compounds. Useful compounds include $PbMoO_4$, $MgWO_4$, $CaMoO_4$, $MnWO_4$, $MnMoO_4$ and the like. In practice, one simply uses pure starting materials such as MoO3, WO3, PbO, CaO, . . . , prepares the exact or near stoichiometric compositions of the compounds for the metallizing compositions, and metallizes at a temperature 50 to 200° C. above the melting points of these compounds.

By varying the metallizing time, the grain-boundary reinforcing compounds penetrate to different depths, according to the square root of time diffusion law. For example, for a liquid diffusion case with a diffusion coefficient of $10^{-5}$ cm×cm/sec, metallizing for 5 to 60 minutes gives a diffusion length or penetration depth of about 0.055 to 0.19 cm. The required liquid metallizing times are 30.2 and 361 seconds, respectively, if a liquid diffusion coefficient of $10^{-4}$ $cm^2/sec$ is used. If the liquid diffusion coefficient of $10^{-5}$ $cm^2/sec$ is chosen, the required metallizing times are 302 and 3,610 seconds, respectively. One can also achieve different penetrations of the reinforcing particles, fibers, or sheets of different penetration depths by changing the metallizing compositions, e.g., from the W-based type to the Mo-based type.

Because of the many benefits of the present inventions, the ceramic metallized coatings and metal-ceramic bonds are thermally stable and useful at high service or use temperatures, e.g., above 630° C., and better than the best Japanese or other bonds. See Prof. Suga's review paper on Japanese ceramic bonding programs referred to above. At these high temperatures, the ceramic coatings or bonds of this invention not only remain solid, but are structurally useful and can carry nominal external loads. Even loads higher than the ceramic's nominal strengths are likely because of the microcomposite and favorable residual stress formations, surface sealing, toughening, and strengthening, and many other techniques described above. By comparison, conventional ceramic coatings contain defects and weak and unstable phases, which become even weaker after the bonding process. These defects or weak phases even become molten, partially molten, or viscous, and cannot, therefore, carry any meaningful external load at high temperatures. Many common ceramic-metal joints fail for these reasons.

As shown in FIGS. 4b–4d, the molten metallized/brazing materials of the metallizing composition not only form the metallized bonding layer to join the metallized ceramic to form bonded ceramic structures, but also penetrate along the ceramic grain boundaries to resolidify and form one-, two-, or three-dimensional metallic reinforcement in the form of hard and strong reinforcing particles, fibers, sheets, branches, particles, roots, or net works. The reinforcement is strengthening to the ceramic if the metallizing/brazing material is relatively hard, such as the various reinforcing compounds of $WO_3$ or $MoO_3$. Toughening materials are ductile and include: Cu, Al, Mg, . . . This toughening is most efficient if the ceramic is thereby compartmentized to prevent stress and strain propagation between compartments within the ceramic.

Alternately, with a different metallizing/brazing composition, the metallic strengthening fibers, sheets, networks, and branches are ductile, yieldable, and made of soft alloys. The strengtheners additionally defines the ceramic grains and completely (FIG. 4d) or partially (FIGS. 4b and 4c) separates the ceramic grains. These soft and ductile ceramic grain boundary materials absorb thermomechanical shocks, making the ceramic less brittle. Through yielding and stress absorption, the thermal mismatch stresses and strains are localized within the enclosed ceramic grain, and cannot transmit to, or propagate into, neighboring grains, at least not with full force. These soft metallic strengtheners thus act as shock absorbers, stress and strain isolators, and ceramic strengtheners or tougheners.

Important forms of these tougheners or yielding metallic components are shown in FIGS. 4a–4d, 7, and 9a–b. Here, these components further separate or divide a large joint or bonded area into compartments so small that the metallic components can restrain or absorb the mismatch stresses and strains within each compartment. These yieldable metallic components prevent the propagation of these stresses and strains into other compartments by minimizing the build-up of these stresses and strains from the entire large area. This "divide-and-conquer" mechanism solves the so-far insolvable problem of thermal mismatch problem in bonded large areas, thereby allowing ceramic bonded structures of any reasonable sizes. Dissimilar material joints meed no longer be limited in size or to CTE match.

The top surfaces of the metallized parts shown in FIGS. 4a–4d have metallized layers whose chemical compositions are the same, or nearly the same, as those of the roots, branches, or networks 41. Since this metal compositions have higher coefficients of thermal expansion than the ceramics 40, mismatch stresses arise on cooling from the high metallizing temperature to room or service temperature. Specifically, the more shrinking, top metal layers will be under tension, compressing and further toughening and strengthening the ceramics 40. A ceramic surface region from 0 to over 200 microns are thus toughened and strengthened through the compression applied by the more shrinking metal layer on the top surface of the metallized ceramics 40. Comparable to the distance between two neighboring roots, branches, or network boundaries, the length or depth of the roots or branches may be from 2 to 200 microns, while the networks may even extend deeper.

Active metals, such as Ti, Zr, Pt, and Nb, and their alloys, with or without other metals such as Ni and Cu, are also useful metallizing materials. But these active metals require pure metals, and perfect vacuum. Otherwise they easily form stable, refractory surface oxides, nitrides, carbides, nitrides, . . . , which are difficult to bond or metallize. Yet, under extremely non-oxidizing conditions, and at processing temperature sufficiently above their melting points to decrease their viscosity, these active metals in perfectly clean, molten form can also wet most ceramics, if both the metal and ceramic are clean with no absorbed oxygen and chemically combined oxides.

Thus, with the new ceramic-ceramic or ceramic-metal joining methods, new structural joints, coatings, or surfaces can be produced that have wide uses due to their hardnesses (diamond, alumina, zirconia), hardness and resistances to wear (diamond, zirconia) or corrosion (diamond, carbon, alumina), electrical or thermal conductivity/insulation (zirconia, beryllia, diamond, silver, stainless steel), catalytic activity (platinum), and other properties or appearances.

Tool bits of silicon carbide or nitride, alumina, diamond, boron carbide, and other cutting or abrasive materials can, for example, be metallized with the methods of the invention and joined to steel holders to form cutting, drilling, milling, grinding, or other machining tools. Particles of the same materials, mixed with the W/Mo metallizing compounds together with copper or nickel brazing alloys, can be spread, as submonolayers, monolayer, or thicker layers, onto inexpensive carbon steel sheets 0.010 to 0.250 inches thick. Upon heating in a reducing atmosphere containing, e.g., hydrogen, a steel sanding sheet or block is formed. The braze metal may be very thin and merely joins the abrasive particles to the steel plate. The same braze metal may have a thickness up to 75–95% of the size of the particles, to support fully and hold strongly these particles while still allowing their sharp cutting edges to perform.

Figure 5:
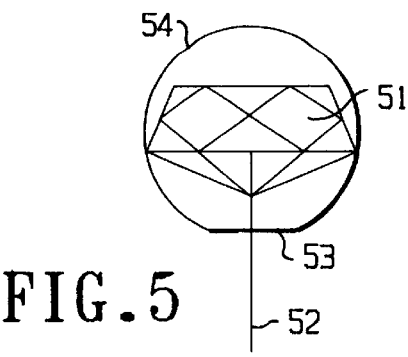
FIG. 5 shows a bonding method for mounting diamond or other gem stones.

Certain gem stones or ceramic tool bits of diamond, sapphire, and quartz can also be mounted onto metal holders. Because of the excellent bond strength, only minimum-contact holding metal is needed, and the ceramic will not be constantly prestressed. As shown in FIG. 5, diamond 51 can now be mounted on the tip of a fine metal wire 52 so that practically its entire back surface can be fully exposed for tool applications, or brilliantly illuminated for gem stones. Also, different back characteristics (color, texture, and reflectivity) can now be instantly changed. This diamond implement is an excellent micromachining (cutting, scribbing, polishing, . . . ) tool which has many sharp points simultaneously exposed that greatly increase the tool life and reduce the tool cost.

Figure 9A:
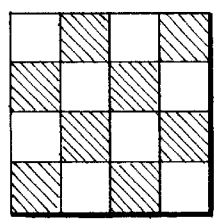
FIGS. 9a–9b show a method of overcoming mismatch stresses on long or large-area coatings or joints.

FIG. 9 shows a method of making large size ceramic coatings on another material or ceramic-bonded joints. The principle is to break the large area, or a long length for a one-dimensional object such as a rod, into many segments so that each segment is of such a small area or length that the mismatch stresses or strains are tolerable by the ceramic. The bonded areas are represented by the white or hatched squares in the chess-board pattern of FIG. 9*a*. The joint or coating in FIG. 9*a* is even vacuum-tight because the corners of the small squares are connected to be gas or vacuum-tight.

Figure 9B:
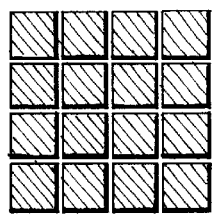

FIG. 9*b* shows another method of making large ceramic coatings or joints. The bonded areas may be the hatched squares, in which case, one side of the joint or coat is fluid communicable with the other side. Alternately, the bonded areas may be the white grid pattern between the squares left by the hatched squares, in which case the joint or coating is again vacuum, gas, or liquid-tight as in the joint or coating of FIG. 9*a*.

A latitude of modification, change and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein described.

The invention, as described above, is not to be construed as limited to the particular forms disclosed herein, since these are to be regarded as illustrative rather than restrictive. Various combinations, equivalent substitutions, or other modifications of the preferred embodiments described herein are obviously possible in light of the description, without departing from the spirit of the invention. In particular, other ceramics such as alumina or zirconia may be used instead of MACOR with the same or a modified metallizing composition. Accordingly, the invention is to be limited only as indicated by the scope of the following appended claims.

What is claimed is:

1. A method of uniformly coating a ceramic onto a substrate to form a ceramic coated product, comprising the steps of:

providing said substrate which is selected from the group consisting of a metal and a ceramic;

providing said ceramic at a selected contact region of said substrate;

providing at said contact region a ceramic coating composition which forms a liquid ceramic coating layer that wets and bonds said ceramic and said substrate when heated to an elevated ceramic coating temperature of over 800° C.;

without pressing or sintering heating said ceramic together with said substrate and said ceramic coating composition to the elevated ceramic coating temperature forming said liquid ceramic coating layer; and solidifying said liquid ceramic coating layer at said contact region into a solid ceramic coating layer uniformly and solidly bonding said ceramic to said substrate thereby producing said ceramic coated product;

said solid ceramic coating layer having such a uniform composition and microstructure as to contain no voids between said ceramic, said substrate visible at a magnification of up to 1000X and is thermodynamically stable at temperatures above 630° C.

2. The method as in claim 1 wherein one of said substrate and said ceramic has a coefficient of thermal expansion which is at least 100% greater than that of the other;

said liquid ceramic coating layer is formed by a liquid diffusion process; and wherein at said elevated ceramic coating temperature said liquid ceramic coating layer wets through surface tension and bonds by chemical reaction both said ceramic and said substrate over substantially 100% of said contact region; and including solidifying through a phase transformation without pressurized sintering said liquid ceramic coating layer into a 100% dense substantially uniformly continuous void-free solid ceramic coating layer which is substantially free of coating defects to retain coating integrity despite a plurality of thermal shocks by quenching to 0° C. from a temperature of at least above 800° C.

3. The method as in claim 1 wherein said solid ceramic coating layer has a maximum thickness of 3.5 mm and consists essentially of an intermetallic compound of said ceramic and a single metal.

4. The method as in claim 1 in which said ceramic coating composition is a ceramic metallizing composition comprising a metal, and including:

forming, without solid sintering under pressure, with a ceramic metallizing composition at least one metallized portion on said ceramic which is adjacent said contact region;

said ceramic-metallizing composition in a liquid form microscopically wetting and sealing crack-initiating ceramic surface voids thereby replacing said crack-initiating ceramic surface voids with solid reinforcing elements to strengthen and toughen the coated ceramic product so that said metallized ceramic surface portion is stronger than the ceramic itself; and adjusting the depth of penetration of said reinforcing elements into the metallized ceramic surface portion by regulating at least one of the following ceramic metallizing parameters: ceramic metallizing composition, metallizing temperature, and metallizing time in the course of forming said ceramic coating layer.

5. The method as in claim 1 further comprising fabricating said ceramic coated product with reinforcing elements solidified from said liquid ceramic coating layer in said ceramic, said reinforcing elements extending from a peripheral surface of said ceramic into the body thereof, said peripheral surface defined by an edge of the ceramic solid at the ceramic coating layer, and at least some of said reinforcements are not parallel to each other.

6. The method as in claim 1 further comprising dividing said solid ceramic coating layer at said contact region into a plurality of laterally adjacent metal-containing load-carrying columns having smaller lateral dimensions than that of said solid ceramic coating layer to thereby reduce maximum thermal mismatch stresses between the substrate and said ceramic;

said smaller lateral dimensions of said metal-containing load-carrying columns being so small that said solid ceramic coating layer can absorb mismatch stresses therein whereby said solid ceramic coating layer can tolerate the reduced maximum thermal mismatch stresses preventing ceramic failures and propagation of these mismatch stresses into neighboring ceramic grains.

7. The method as in claim 1 wherein:

said substrate providing step comprises supplying a porous ceramic material with interconnected pores having internal surfaces; and said ceramic coating composition on heating to the ceramic coating temperature forms, said liquid ceramic coating layer that wets and covers substantially 100% of said internal surfaces.

8. The method in claim 1 including:

forming the ceramic coating composition by suspending a plurality of mixed ceramic coating composition powders of differing compositions and densities in a fluid suspension medium; and wherein differences in settling velocities in the fluid suspension medium of said mixed powders are minimized by ensuring that dense powder particles have smaller diameters relative to the diameters of powder particles that are less dense.

9. The method as in claim 2 including using a metallizing and brazing solution diluted to less than 0.1 mols per liter to form, through phase change without solid sintering under pressure, said solid coated ceramic coating layer which has a maximum thickness of no more than 3.5 mm.

10. The method as in claim 1 wherein said heating step comprises laser pulse heating for less than a second in a selected ambient.

11. The method as in claim 1 using a single-step elevated temperature ceramic coating procedure with a combined metallizing and brazing solution diluted to less than 0.1 moles per liter so that said solid coated ceramic layer has a maximum thickness which is within 1000 Å of a specified thickness value of no more than about 3.5 mm.

12. The method as in claim 1 wherein said solid ceramic coating layer is, atom to atom, bonded to said ceramics so free of bonding defects as to be practically useful above a temperature of about 850° C.

13. The method of coating a ceramic onto a substrate comprising;

supplying said ceramic;

selecting a metal or ceramic substrate having a top major surface;

preparing a ceramic coating composition containing a material chemically reactive to said ceramic;

causing said ceramic coating composition to contact at least one of said substrate and said ceramic;

heating the substrate, ceramic, and ceramic coating composition to an elevated temperature of over 800° C. without externally applied pressure to form on said substrate a metallizing fluid ceramic coating layer comprising a material of said ceramic;

said fluid ceramic coating layer, wetting and bonding by chemical reaction both said ceramic and said substrate at said elevated temperature; and including solidifying through a phase transformation said fluid ceramic coating layer into a solid ceramic coating layer which is sufficiently free of coating defects to withstand at least a plurality of thermal shocks by quenching to 0° C. water from a temperature of at least 630° C.

14. The method as in claim 13 wherein:

said ceramic comprises a plurality of selected ceramic particles; and said heating step comprises applying a temperature gradient normally of said top major surface of said substrate to sequentially form, by solidification and not by pressurized sintering, sub-layer by sub-layer starting from said top major surface upward, a coated solid ceramic layer of said selected ceramic particles;

said solid coated ceramic layer growing elongated ceramic grains normally of the top major surface of said substrate.

15. The method as in claim 14 wherein said plurality of ceramic particles is a ceramic superconducting material selected from the group consisting of copper oxide, barium oxide, yttrium oxide, calcium oxide, tellurium oxide, and a mixture thereof.

16. The method as in claim 13 wherein said substrate is selected from the group consisting of Mo, Ni, Si, Fe, W, SiC, diamond, boron nitride, and ceramic superconductor, and mixtures thereof; and said ceramic is a plurality of elongated ceramic grains having substantially uniform solidified ceramic layer thickness of less than a value selected from the group consisting of 1 micron, 1,000 A, and 100 A with a controlled accuracy of less than 100 or 10 Å in said bonding layer thickness, terminating into a common coplanar outer surface having a planarity accuracy of better than one micron to facilitate mounting of a precision component thereon, at least a plurality of said elongated grains having a length/width or aspect ratio of over 3.

17. A method of uniformly coating onto a substrate mixed solid particles having different average densities and sizes and suspended in a common fluid suspension medium comprising:

size-rationing said mixed solid particles having the different average densities and sizes in at least one calculated ratio to equalize, with an accuracy of better than 10 to 20%, average settling velocities of said mixed solid particles in said common fluid suspension medium at least in a preselected time period of the coating process, at least some of said mixed solid particles being non-metallic particles;

suspending said mixed solid particles in said common fluid suspension medium to form a coating composition;

applying said coating composition onto the substrate to form a substantially uniform coating of said mixed solid particles at least in the preselected time period of the coating process whereby said mixed solid particles come out of said fluid suspension medium in a substantially constant chemical composition ensuring uniformity and reproducibility of the coating results; and heating said substrate and the coating of said mixed solid particles suspension thereon to an elevated heat treatment temperature to form a uniformly coated mixed solid particles product.

18. A method of forming a uniform and continuous coated ceramic layer on a substrate, comprising;

supplying a substrate;

providing a plurality of ceramic particles on said substrate, one of said ceramic particles and substrate having a coefficient of thermal expansion which is over 100% higher than that of the other;

forming said ceramic particles on said substrate in a layer form wherein neighboring ceramic particles have respective contact regions therebetween;

providing at each of said contact regions a ceramic coating composition capable of forming a uniform and continuous fluid ceramic coating layer that fluidizes when heated to an elevated ceramic coating temperature of over 800° C.;

without application of external pressure heating together said substrate, said ceramic particles and said ceramic coating composition to the elevated ceramic coating temperature forming said fluid ceramic coating layer which wets and bonds by chemical reaction said ceramic particles and said substrate at said respective contact regions; and solidifying through a phase transformation said fluid ceramic coating layer to produce a uniform and continuous solid coated ceramic layer on said substrate;

said solid coated ceramic layer being thermally stable at a temperature of at least above 630° C.

19. The method as in claim 18 further comprising:

forming said uniform and continuous fluid coating ceramic layer onto a mismatched substrate differing in coefficient of thermal expansion from that of said ceramic layer by at least 100%;

laterally dividing said solid coated ceramic layer into a plurality of smaller laterally separated but adjacent coated ceramic regions with peripheral spaces therebetween; and providing a yieldable metallic material to completely fill the peripheral spaces to avoid ceramic failures by reducing, due to the smaller coated ceramic region sizes, thermal mismatch stresses between said coated ceramic regions and said substrate.

20. The method as in claim 18 wherein at said elevated ceramic coating temperature said fluid ceramic coating layer uniformly wets said substrate without external pressure, and said coated ceramic layer being sufficiently free of coating defects to retain coating integrity despite a plurality of thermal shocks by quenching to 0° C. from a temperature of at least above 630° C.

21. The method as in claim 18 wherein said uniform and continuous solid coated ceramic layer is at least ¼ inches (6.35) mm in a lateral dimension thereof; said solidifying step comprising introducing favorable compressive residual thermal mismatch stress into the solid coated ceramic layer for resisting thermal mismatch stress between said substrate and said solid coated ceramic layer.

22. The method as in claim 18 wherein said solid coated ceramic e layer has a maximum thickness of no more than 3.5 mm and said heating step comprises stabilizing, preaging, and burning-in said solid coated ceramic layer.

23. The method as in claim 18 wherein said solid coated ceramic layer contains no voids or cracks visible at magnification of up to 1000X at said respective contact regions between said ceramic particles thereby retaining mechanical strength without failure even after quenching into a fluid medium at 0° C. from above 630° C.

24. The method as in claim 18 further comprising:

supplying said substrate to have a top major surface; and selected from the group consisting of diamond, alumina, Ni, Fe, Si, Mo, W, zirconia, boron carbide, BN, SiC silicon consisting zirconium carbide, TiB, TiC and combinations thereof; and forming said uniform and continuous fluid ceramic coating layer onto said top major surface of said substrate;

processing in a neutral to reducing gaseous environment containing hydrogen at an ambient pressure of no more than 760 mm mercury, at the elevated ceramic coating temperature of no more than about 900° C. with a processing temperature gradient applied normally of top major surface of said substrate so that the processing temperature of said fluid ceramic coating layer increases upwardly with distance from the top major surface whereby through a phase transformation by solidification without solid sintering under pressure said solid coated ceramic layer is formed by freezing crystallization of said fluid ceramic coating layer into elongated ceramic polycrystalline grains oriented substantially normally of the top major surface of said substrate;

said elongated ceramic grains being substantially uniform in layer thickness of less than a value selected from the group consisting of 1 micron, 1,000 Å, and 100 Å with a controlled accuracy is said layer thickness of less than 100 or 10 Å and having a common length to all terminate into a common planar outer surface having a planarity accuracy of less than 1 micron.

25. A method of uniformly coating a plurality of ceramic particles onto a substrate to form a solid ceramic coated product wherein one of said substrate and said ceramic particles has a coefficient of thermal expansion which is at least 100% greater than that of the other, comprising the steps of:

providing a substrate which is selected from the group consisting of a metal and a ceramic and having a contact region thereon;

without application of external pressure, providing at said contact region a fluid ceramic coating composition capable of forming a fluid ceramic bonding layer positioned at least between said substrate and said ceramic particles when heated to an elevated ceramic coating temperature;

heating said substrate, said ceramic particles, and said fluid ceramic coating composition to the elevated ceramic coating temperature forming said fluid ceramic bonding layer;

said fluid ceramic layer, wetting by chemical reaction and not by plating or solid sintering under pressure, the plurality of said ceramic particles and said substrate to form a fluid ceramic coating layer; and solidifying through a phase transformation said fluid ceramic bonding layer into a solid ceramic coating layer thereby producing said solid ceramic coated product;

said solid ceramic coating layer containing no voids or cracks visible at a magnification of up to 10000X, and being capable of withstanding a temperature of at least 630° C.

26. The method as in claim 25 wherein said solid ceramic coating layer has a maximum thickness which is within 1000 A of a specified thickness value of no more than about 3.5 mm.

27. The method of claim 25 wherein said solidifying step comprises cooling in a single direction beginning with and normally of said contact region and continuing in a direction normally of and away from the contact region to produce elongated solid ceramic grains oriented in the direction of cooling;

at least a majority of said solid elongated ceramic grains having a substantially uniform width of no more than 1 micron and a length of at least 3.5 mm.

28. The method as in claim 27 wherein said solidified ceramic coating layer has a lateral dimension of at least 6.35 mm, said ceramic particles are elongated and strengthened ceramic grains having substantially uniform sizes oriented normally of a top major surface of said substrate; and uniform lengths to an accuracy of better than 1 micron.

29. The method as in claim 25 wherein said heating step comprises providing a ceramic coating environment at a temperature of no more than 1200° C. and comprising a reducing gas and a carbon containing gas;

said reducing gas comprising hydrogen and said carbon-containing gas comprising a gaseous material selected from the group consisting of methane and propane.

30. A method of making a heat-resistant article of manufacture formed of a ceramic and a substrate comprising the steps of:

providing said ceramic;

providing a substrate which is selected from the group consisting of a metal and a ceramic and having at a selected area thereon a contact region;

providing at said contact region a ceramic coating composition which forms a fluid ceramic coating layer that is positioned at least between said ceramic and said substrate when heated to an elevated ceramic coating temperature; and heating without external pressure or sintering said ceramic together with said substrate and said ceramic coating composition to the elevated ceramic coating temperature forming said fluid ceramic coating layer which fluid diffusion bonds together through chemical reaction said ceramic and said substrate;

solidifying through a phase transformation said fluid diffusion bonded substrate-ceramic assembly to produce a solid ceramic coated article;

said ceramic coating layer containing no voids or cracks visible at a magnification of up to 1000× said ceramic coating layer and being sufficiently free of coating defects to retain coating integrity despite a plurality of thermal shocks by quenching from a temperature of at least 630° C. whereby said solid ceramic coated article of manufacture can also withstand temperatures above 630° C.

* * * * *